United States Patent [19]

Walser

[11] Patent Number: 5,015,661
[45] Date of Patent: May 14, 1991

[54] CHROMANES AND THEIR PHARMACEUTICAL COMPOSITIONS AND METHODS

[75] Inventor: Armin Walser, West Caldwell, N.J.
[73] Assignee: Hoffmann-La Roche Inc., Nutley, N.J.
[21] Appl. No.: 367,082
[22] Filed: Jun. 16, 1989

Related U.S. Application Data

[63] Continuation-in-part of Ser. No. 230,094, Aug. 9, 1988, abandoned.

[51] Int. Cl.$^5$ .................. A61K 31/355; C07D 311/72
[52] U.S. Cl. .................................. 514/443; 514/230.5; 514/256; 514/307; 514/314; 514/337; 514/374; 514/397; 514/414; 514/444; 514/458; 544/99; 544/101; 544/105; 544/331; 546/147; 546/152; 546/148; 546/174; 546/269; 548/235; 548/236; 548/454; 549/58; 549/60; 549/408; 549/410
[58] Field of Search ............... 546/269, 147, 148, 152, 546/174; 549/58, 60, 408, 410; 544/99, 101, 105, 331; 548/235, 236, 454; 514/337, 443, 444, 458, 230.5, 256, 307, 314, 374, 397, 414

[56] References Cited

U.S. PATENT DOCUMENTS

| 4,572,912 | 2/1986 | Yoshioka et al. | 514/369 |
| 4,694,090 | 9/1987 | Shiono et al. | 549/407 |
| 4,752,646 | 6/1988 | Cohen | 549/408 |
| 4,824,971 | 4/1989 | Cohen | 549/408 |
| 4,879,395 | 11/1989 | Coffen et al. | 549/408 |
| 4,914,217 | 1/1989 | Ka-kong Chan et al. | 549/398 |

FOREIGN PATENT DOCUMENTS

| 180190-A | 10/1985 | European Pat. Off. . |
| 61148173-A | 12/1984 | Japan . |
| 61-204122-A | 3/1985 | Japan . |
| 61-267570-A | 5/1985 | Japan . |
| 61-267571-A | 5/1985 | Japan . |
| 61-210030A | 9/1986 | Japan . |
| 62-132879 | 6/1987 | Japan . |

OTHER PUBLICATIONS

Chem. Abstracts, vol. 112 (13), 118862s (1990).

Primary Examiner—Mary C. Lee
Assistant Examiner—Bernard I. Dentz
Attorney, Agent, or Firm—George M. Gould; Bernard S. Leon; William G. Isgro

[57] ABSTRACT

Racemic Compounds of the formula

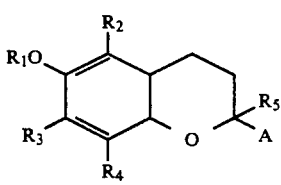

A is $—C\equiv C—R_6$, $—CH_2—CH_2—R_7$ or

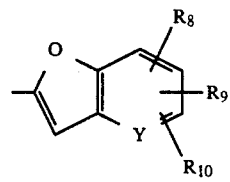

$R_1$ is hydrogen or lower alkanoyl,
$R_2$, $R_3$, and $R_4$ independently are hydrogen or lower alkyl,
$R_5$ is lower alkyl,
$R_6$ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl lower alkoxy, lower alkanoyl, lower alkanoyloxy, hydroxy-lower alkyl, carboxy, lower alkoxycarbonyl, hydroxyimino lower alkyl, amino, amino lower alkyl, mono- or di-lower alkylamino, mono- or di-lower alkylamino-lower alkyl, lower alkanoylamino, aminocarbonyl, lower alkylaminocarbonyl, lower dialkylaminocarbonyl, trifluoroacetylamino, trifluoromethyl, hydroxy, pyridyl, or on adjacent carbons can be

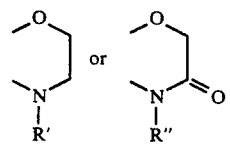

wherein R' is hydrogen, lower alkanoyl, trifluoroacetyl and R" hydrogen or lower alkyl,
$R_7$ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl-lower alkoxy of 2-7 carbon atoms, lower alkanoyl, lower alkanoyloxy, hydroxy-lower alkyl, carboxy, lower alkoxycarbonyl, amino, amino-lower alkyl, mono- or di-lower alkylamino, mono- or di-lower alkylamino-lower alkyl, lower alkanoylamino, aminocarbonyl, lower alkylaminocarbonyl, lower dialkylaminocarbonyl, trifluoroacetylamino, trifluoromethyl, hydroxy or pyridyl, or on adjacent carbons can be

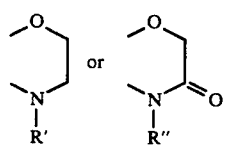

wherein R' is hydrogen, lower alkanoyl, trifluoroacetyl and R" hydrogen or lower alkyl,
$R_8$, $R_9$, $R_{10}$, independently, are hydrogen, hydroxy, (Abstract continued on next page.)

lower alkyl, lower alkoxy, hydroxy lower alkyl, fluorine, chlorine or lower alkanoyl provided that no more than one of $R_8$, $R_9$, and $R_{10}$ is hydroxy, lower alkoxy, lower hydroxyalkyl, fluorine, chlorine or lower alkanoyl, and Y is CH or N, and their enantiomer and salts thereof are described.

The compounds of formula I exhibit activity as inhibitors of 5-lipoxygenase and inhibit lipid peroxidation. They are, therefore, useful in the treatment of diseases caused or aggravated by excess oxidative metabolism of arachidonic acid via the 5-lipoxygenase pathway and in the treatment of inflammation, arthritis, allergies, asthma and psoriasis. The compounds of formula I can also be used to prevent peroxidation of lipids and thus protect lipid membranes from oxidative stress.

30 Claims, No Drawings

CHROMANES AND THEIR PHARMACEUTICAL COMPOSITIONS AND METHODS

CROSS-REFERENCE TO RELATED APPLICATIONS

This application is a continuation in-part of U.S. Patent application No. 230,094, filed Aug. 9, 1988 now abandoned.

BRIEF DESCRIPTION OF THE INVENTION

The invention relates to racemic compounds of the formula

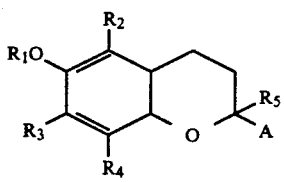

I

A is —C≡C—$R_6$, —$CH_2$—$CH_2$—$R_7$ or

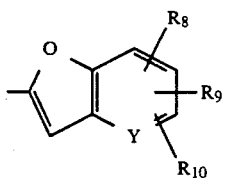

$R_1$ is hydrogen or lower alkanoyl, $R_2$, $R_3$, and $R_4$ independently are hydrogen or lower alkyl.

$R_5$ is lower alkyl, $R_6$ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl lower alkoxy, lower alkanoyl, lower alkanoyloxy, lower hydroxyalkyl, carboxy, lower alkoxycarbonyl, hydroxyimino lower alkyl, amino, amino-lower alkyl, mono- or di- lower alkylamino, mono- or di-lower alkylamino-lower alkyl, lower alkanoylamino. aminocarbonyl, lower alkylaminocarbonyl, lower dialkylaminocarbonyl, trifluoroacetylamino, trifluoromethyl, hydroxy, pyridyl, or on adjacent carbons can be

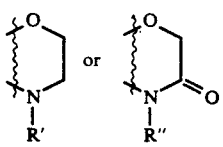

wherein R' is hydrogen, lower alkanoyl, trifluoroacetyl and R" hydrogen or lower alkyl, $R_7$ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl-lower alkoxy of 2-7 carbon atoms, lower alkanoyl, lower alkanoyloxy, lower hydroxyalkyl, carboxy, lower alkoxycarbonyl, amino, amino-lower alkyl, mono- or di-lower alkylamino, mono- or di-lower alkylamino-lower alkyl, lower alkanoylamino, aminocarbonyl, lower alkyaminocarbonyl, lower dialkylaminocarbonyl, trifluoroacetylamino, trifluoromethyl hydroxy or pyridyl or on adjacent carbons can be

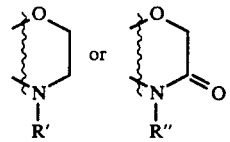

wherein R' is hydrogen, lower alkanoyl, trifluoroacetyl and R" hydrogen or lower alkyl, $R_8$, $R_9$, and $R_{10}$, independently, are hydrogen, hydroxy, lower alkyl lower alkoxy, lower hydroxyalkyl, fluorine, chlorine or lower alkanoyl provided that no more than one of $R_8$, $R_9$, and $R_{10}$ is hydroxy, lower alkoxy, lower hydroxyalkyl, fluorine, chlorine or lower alkanoyl, and Y is CH or N, and their enantiomers and salts thereof.

The compounds of formula I exhibit activity as inhibitors of 5-lipoxygenase and inhibit lipid peroxidation. They are, therefore, useful in the treatment of diseases caused or aggrevated by excess oxidative metabolism of arachidonic acid via the 5-lipoxygenase pathway and in the treatment of inflammation, arthritis. allergies, asthma and psoriasis. The compounds of formula 1 can also be used to prevent peroxidation of lipids and thus protect lipid membranes from oxidative stress.

DETAILED DESCRIPTION OF THE INVENTION

As used herein, the term "lower alkyl", denotes a straight or branched chain saturated hydrocarbon containing 1 to 7 carbon atoms, preferably from 1 to 4 carbon atoms, for example, methyl, ethyl, propyl, isopropyl, butyl, t-butyl, neopentyl pentyl, heptyl an the like. The term "lower alkoxy" denotes an alkyl ether group in which the alkyl group is as described above, for example, methoxy, ethoxy, propoxy, pentoxy and the like.

The terms "lower alkanoyl" and "lower alkanoyloxy" preferably denote an alkanoyl or alkanoyloxy group of 1 to 7 carbon atoms. preferably from 1 to 4 carbon atoms, for example, formyl, acetyl, propanoyl, butanoyl and the like, and formyloxy, acetoxy, propanoyloxy and the like, respectively.

The term "lower hydroxylalkyl" denotes a lower alkyl radical of 1 to 7 carbon atoms which bears a hydroxyl group as substituent.

The term "hetereoaromatic radical" denotes a monocyclic 5 or 6-membered hetereocyclic or a bicyclic hetereocyclic aromatic radical containing one or more hetero atoms, selected from nitrogen, oxygen and sulfur, which radical may optionally be substituted by one or two lower alkyl, lower alkoxy groups, chlorines or fluorines. It is understood that heterocyclic refers to a carbocyclic moiety in which one or more of the carbons are replaced, independently, by oxygen, nitrogen or sulfur.

As used herein, and as is evident from the nomenclature and structures utilized throughout the specification, the structural representation ═ is equivalent to —CH═CH and ≡ is —C≡C—.

The invention relates to racemic compounds of the formula

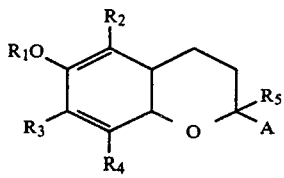

A is —C≡C—R₆, —CH₂—CH₂—R₇ or

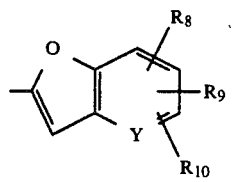

R₁ is hydrogen or lower alkanoyl,
R₂, R₃, and R₄ independently are hydrogen or lower alkyl,
R₅ is lower alkyl,
R₆ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl lower alkoxy, lower alkanoyl, lower alkanoyloxy, lower hydroxyalkyl, carboxy, lower alkoxycarbonyl, hydroxyimino lower alkyl, amino, lower alkanoylamino, aminocarbonyl, lower alkylaminocarbonyl, lower dialkylaminocarbonyl, trifluoroacetylamino, trifluoromethyl, hydroxy, pyridyl, or on adjacent carbons can be

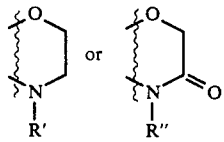

wherein R' is hydrogen, lower alkanoyl, trifluoroacetyl and R" hydrogen or lower alkyl,
R₇ is a heteroaromatic radical or an aromatic radical selected from phenyl, naphthyl or phenanthryl, which aromatic radical may optionally be substituted by one or more substituents selected from chlorine, fluorine, lower alkyl, lower alkoxy, phenyl-lower alkoxy of 2-7 carbon atoms, lower alkanoyl, lower alkanoyloxy, lower hydroxyalkyl, carboxy, lower alkoxycarbonyl, amino amino-lower alkyl, mono- or di-lower alkylamino, mono. or di-lower alkylamino-lower alkyl, lower alkanoylamino aminocarbonyl, lower alkyaminocarbonyl, lower dialkylaminocarbonyl, trifluoroacetylamino, trifluoromethyl, hydroxy or pyridyl, or on adjacent carbons can be

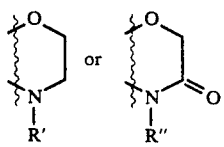

wherein R' is hydrogen, lower alkanoyl, trifluoroacetyl and R" hydrogen or lower alkyl,
R₈, R₉, and R₁₀, independently, are hydrogen, hydroxy, lower alkyl, lower alkoxy, lower hydroxyalkyl, fluorine, chlorine or lower alkanoyl provided that no more than one of R₈, R₉, and R₁₀ is hydroxy, lower alkoxy, lower hydroxyalkyl, fluorine, chlorine or lower alkanoyl, and Y is CH or N, and their enantiomers and salts thereof.

Exemplary of 5- or 6- membered aromatic heteromonocyclic or bicyclic radicals are pyridinyl, imidazolyl, thienyl, 2-(pyridyl)thienyl, 2-(phenyl)thienyl, 2-chlorothienyl, furyl, pyrimidinyl, oxazolyl, quinolinyl, isoquinolinyl, indolyl, benzothienyl, benzofuranyl, or the like.

A preferred group of the compounds of formula I comprises those wherein R₁ is hydrogen, R₂-R₅ are methyl and A is —C≡C—R₆ or

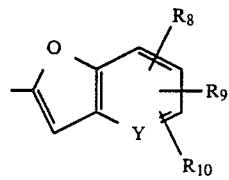

A more preferred group of the compounds of formula I are those wherein R₁ is hydrogen, R₂-R₅ are methyl and A is —C≡C—R₆.

Another more preferred group of the compounds of formula I comprises those wherein R₁ is hydrogen. R₂-R₅ are methyl and A is

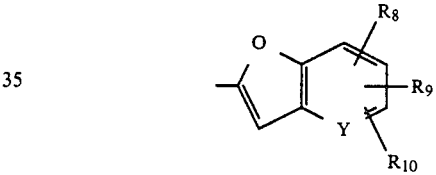

A still more preferred group is the compounds of formula I comprises those wherein R₁ is hydrogen, R₂-R₅ are methyl and A is —C≡C—R₆ wherein R₆ is unsubstituted phenyl, thienyl, benzothienyl or pyridinyl or substituted phenyl.

Another still more preferred group is the compounds of formula I comprises those wherein R₁ is hydrogen. R₂-R₅ are methyl and A is

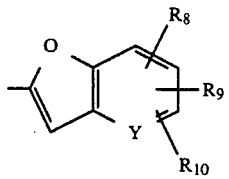

wherein Y is N and R₈ and R₉, independently are hydrogen or lower alkyl

Most preferred compounds are:
R-[2-(Benzo[b]thiophen-3-yl)ethynyl]-3,4-dihydro-2,5,7,8-tetramethyl-2H-1-benzopyran-6-ol
S-[2-(Benzo[b]thiophen-3-yl)ethynyl]-3,4-dihydro-2,5,7,8-tetramethyl-2H-1-benzopyran-6-ol
rac-[2-(Benzo[b]thiophen-3-yl)ethynyl]-3,4-dihydro-2,5,7,8-tetramethyl-2H-1-benzopyran-6-ol
R-3,4-Dihydro-2,5,7,8-tetramethyl-2-[(2-thienyl)ethynyl]-2H-1-benzopyran-6-ol S-3,4-Dihydro-2,5,7,8-tetramethyl-2-[(2-thienyl)ethynyl]-2H-1-benzopyran-6-ol
rac-3,4-Dihydro-2,5,7,8-tetramethyl-2-[(2-thienyl)ethynyl]-2H-1-benzopyran-6-ol
rac-3,4-Dihydro-2-(furyl[3,2-b]pyridin-2-yl)-2,5,7,8-tetra-methyl-2H-1-benzopyran-6-ol
rac-2-(2-Benzofuranyl)-3,4-dihydro-2,5,7,8-tetramethyl-2H-1-benzopyran-6-ol; and
rac-3,4-Dihydro-6-hydroxy-2,5,7,8-tetramethyl-2H-1-benzopyran-2-yl)-7-methoxybenzofuran-5-methanol;
Other preferred compounds are:
rac-[2-(Benzo[b]thiophen-2-yl)ethynyl]-3,4-dihydro-2,5,7,8- 7,8 tetramethyl-2H-1-benzopyran-6-ol;
rac-3,4-Dihydro-2,5,7,8-tetramethyl-2-[2-(3-pyridinyl)ethynyl]-2H-1-benzopyran-6-ol;
rac-3,4-Dihydro-2,5,7,8-tetramethyl-2-(2-phenylethyl)-2H-1-benzopyran-6-ol;
rac-3,4-Dihydro-2,5,7,8-tetramethyl-2-(2-phenylethynyl)-2H-1-benzopyran-6-ol;
rac-3,4-Dihydro-2,5,7,8-tetramethyl-2-[2-(2-thienyl)ethyl]-2H-1-benzopyran-6-ol;
rac-4-[2-(3,4-Dihydro-6-hydroxy-2,5,7,8-tetramethyl-2H-1-benzopyran-2-yl)ethyl]-1,2-benzenediol;
rac-3,4-Dihydro-2,5,7,8-tetramethyl-2-[2-(3-pyridinyl)ethyl]-2H-1-benzopyran-6-ol;
rac-3,4-Dihydro-2,5,7,8-tetramethyl-2-[2-(2-pyridinyl)ethyl]-2H-1-benzopyran-6-ol;
rac-3,4-Dihydro-2-(5-methylfuro[3,2-b]pyridin-2-yl)-2,5,7,8-tetramethyl-2H-1-benzopyran -6-ol; and
rac-2-(3,4-Dihydro-6-hydroxy-2,5,7,8-tetramethyl-2H-1-benzo-pyran-2-yl)-7-methoxy-5-benzofurancarboxaldehyde;
Additional exemplary compounds of formula I are:
rac-3,4-Dihydro-2,5,7,8-tetramethyl-2-(2-hydroxyphenyl-ethynyl)-2H-1-benzopyran-6-ol;
rac-3,4-Dihydro-2-[(4-hydroxy-3-propylphenyl)ethynyl]- 2,5,7,8-tetramethyl-2H-1-benzopyran-6-ol;
rac-[(3-Acetyloxy-4-methoxyphenyl)ethynyl]-3,4-dihydro-2,5,7,8-tetramethyl-2H-1-benzopyran-6-ol;
rac-5-[(3,4-Dihydro-6-hydroxy-2,5,7,8-tetramethyl-2H-1 -benzopyran-2yl)ethynyl]-2-hydroxybenzoic acid methyl ester;
rac-3,4-Dihydro-2,5,7,8-tetramethyl-2-{[5-(2-pyridinyl)-2thienyl]ethynyl}-2H-1-benzopyran-6-ol;
rac-3,4-Dihydro-2,5,7,8-tetramethyl-2-{[4-(3-pyridinyl)-phenyl]ethynyl}-2H-1-benzopyran -6-ol;
rac-3,4-Dihydro-2,5,7,8-tetramethyl-2-[(2-pyridinyl)-ethynyl]-2H-1-benzopyran-6-ol;
rac-2-[(5-Butyl-2-thienyl)ethynyl]-3,4-dihydro-2,5,7,8-tetra-methyl-2H-1-benzopyran-6-ol;
rac-3,4-Dihydro-2,5,7,8-tetramethyl-2-[(3-quinolinyl)-ethynyl]-2H-1-benzopyran-6-ol;
rac-3,4-Dihydro-2,5,7,8-tetramethyl-2-[(1-naphthalenyl) ethynyl]-2H-1-benzopyran-6-ol;
rac-2-{[3-Acetyloxy-4-(phenylmethoxy)phenyl]ethynyl}-3,4-dihydro-2,5,7,8-tetramethyl-2H--1-benzopyran-6ol;
rac-3,4-Dihydro-2-{[3-hydroxy-4-(phenylmethoxy)-phenyl]-ethynyl}-2,5,7,8-tetramethyl-2H-1-benzopyran-6-ol;
rac-2-[(3-Acetyloxy-4-methoxyphenyl)ethyl]-3,4-dihydro-2,5,7,8-tetramethyl-2H-1-benzopyran-6-ol;
rac-3,4-Dihydro-2,5,7,8-tetramethyl-2-{[4-(3-pyridinyl)-2-phenyl]ethyl}-2H-1-benzopyran-6-ol;
rac-3,4-Dihydro-2,5,7,8-tetramethyl-2-{[5-(2-pyridinyl)-2-thienyl]ethyl}-2H-1-benzopyran-6-ol;
rac-4-[2-(3,4-Dihydro-6-hydroxy-2,5,6,7,8-tetramethyl-2H-1-benzopyran-2-yl)ethyl]-1,2-benzenediol-2-acetate;
rac-{2-[5-(Aminomethyl)-2-hydroxy-3-methoxyphenyl-]ethyl}-3,4-dihydro-2,5,7,8-tetramethyl-2H-1-benzopyran-6-ol hydrochloride;
rac-1-[2-(3,4-Dihydro-6-hydroxy-2,5,7,8-tetramethyl-2H-1-benzopyran-2yl)-6-hydroxy 7-propylbenzofuran-5 yl]ethanone;
rac-3-[(3,4-Dihydro 6-hydroxy-2,5,7,8-tetramethyl-2H-1 -benzo-pyran-2-yl)ethynyl]-4-hydroxy-5-methoxybenzaldehyde;
rac-3-[(3,4-Dihydro-6-hydroxy-2,5,7,8-tetramethyl-2H-1-benzo-pyran-2-yl)ethynyl]-4-hydroxy-5-methoxybenzaldehyde oxime;
rac-3-[(3,4-Dihydro-6-hydroxy-2,5,7,8-tetramethyl-2H-1-benzo-pyran-2-yl)ethynyl]-4-hydroxy-5-methoxybenzenemethanol;
rac-2-[(2-Aminophenyl)ethynyl]-3,4-dihydro-2,5,7,8-tetra-methyl-2H-1-benzopyran-6-ol;
rac-2,2,2-Trifluoro-N-{2-[(3,4-dihydro-2,5,7,8-tetramethyl2H-1-benzopyran-2-yl)ethynyl]-phenyl}acetamide;
rac-3,4-Dihydro-2-[(3-methoxyphenyl)ethynyl]-2,5,7,8-tetra-methyl-2H-1 benzopyran-6-ol;
rac-2-{[3-(Trifluoromethyl)phenyl]ethynyl}-3,4-dihydro-2,5,7,8-tetramethyl-2H-1-benzopyran-6-ol;
rac-2-[(3,4-Difluorophenyl)ethynyl]-3,4-dihydro-2,5,7,8-tetramethyl-2H-1-benzopyran-6-ol;
rac-3,4-Dihydro-2-[(4-isoquinolinyl)ethynyl]-2,5,7,8-tetra-methyl-2H-1-benzopyran-6-ol;
rac-3,4-Dihydro-6-[(3,4-dihydro-6-hydroxy-2,5,7,8 tetramethyl-2H-1-benzopyran-2-yl) ethynyl]-4-(trifluoroacetyl)-2H-1,4-benzoxazine.
rac-2-[(3,4-Dihydro-2H-1,4-benzoxazin-6-yl)ethynyl]3,4-dihydro-2,5,7,8-tetramethyl-2H-1-benzopyran-6-ol hydrochloride hydrate;
rac-[(3,4-Dihydro-6-hydroxy-2,5,7,8-tetramethyl-2H 1-benzo-pyran-2-yl)ethynyl]-4-methyl-2H-1,4-benzoxazin-3(4H)-one;
rac-3,4-Dihydro-2-[2-(3-methoxyphenyl)ethyl]-2,5,7,8-tetra-methyl-2H-1-benzopyran-6-ol;
rac-2-[2-(5-Butyl-2-thienyl)ethyl]-3,4-dihydro-2,5,7,8-tetramethyl-2H-1-benzopyran-6-ol;
rac-5-[2-(3,4-Dihydro-6-hydroxy-2,5,7,8-tetramethyl-2H-1-benzopyran-2-yl)ethyl]-2hydroxybenzoic acid methyl ester; and the like.

The compounds of formula I can be prepared as hereinafter described in Reaction Schemes I, II, III, IV and V.

Reaction Scheme I

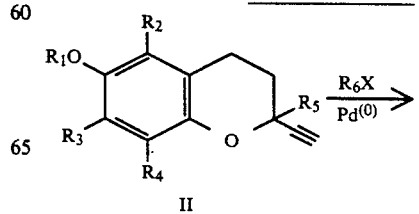

-continued
Reaction Scheme I

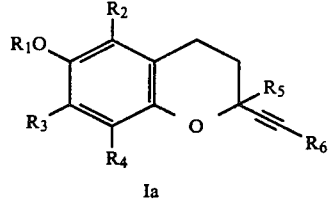

wherein $R_1$, $R_2$, $R_3$, $R_4$, $R_5$ and $R_6$ are as previously described, and x is bromine, iodine or trifluorosulfonyloxy In Reaction Scheme I, a compound of formula II as a racemate or one of its enantiomers, the racemates are known compounds or can be prepared according to known procedures, is converted to the corresponding compound of formula Ia by reacting with a compound of the formula $R_6X$ in the presence of palladium catalyst, for example, bis(triphenylphosphine)palladium dichloride or diacetate and in the presence of an excess of a proton acceptor, for example, triethylamine and optionally in an inert organic solvent, for example, acetonitrile, tetrahydrofuran, dimethylformamide or the like, at a temperature in the range of from about room temperature to about 100° C.

The resulting compound of formula Ia can be recovered utilizing known procedures, for example, crystallization, distillation, chromatography and the like.

Reaction Scheme II

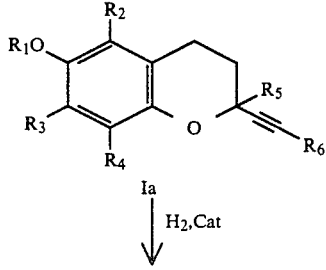

-continued
Reaction Scheme II

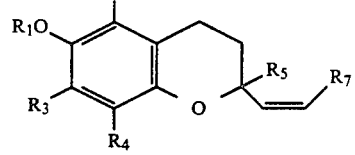

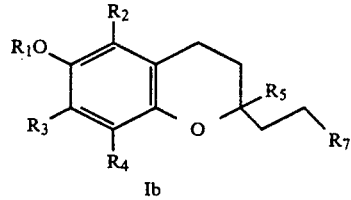

wherein $R_1$, $R_2$, $R_3$, $R_4$, $R_5$, $R_6$ and $R_7$ are as previously described.

In reaction Scheme II, a compound of formula Ia, is hydrogenated utilizing for example, a noble metal catalyst such as, palladium, platinum or nickel and hydrogen, to give the corresponding compound of formula Ib. The reaction is carried out conveniently in the presence for an inert solvent, for example, an alkanol, such as, ethanol, or ether, such as, tetrahydrofuran or the like, acetic acid or the like at a temperature in the range of from about room temperature to about 50° C., and at a pressure of from about 1 atm. to about 20 atms., preferably at atmospheric pressure.

A compound of formula Ib can be recovered utilizing known procedures, for example, crystallization, chromatography and the like.

It is noted that the compound of formula III which is formed therewith during the hydrogenation, can in fact be prepared by utilizing a Lindlar catalyst or palladium on carbon in the presence of a catalyst poison, such as, thiophene, and thereafter recovered by chromatography or crystallization.

Reaction Scheme III

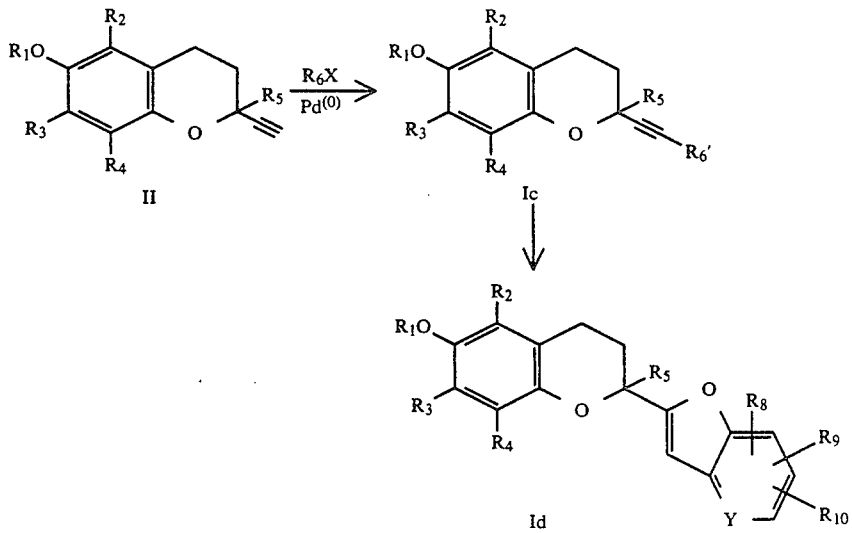

wherein $R_6'$ is

Reaction Scheme IV

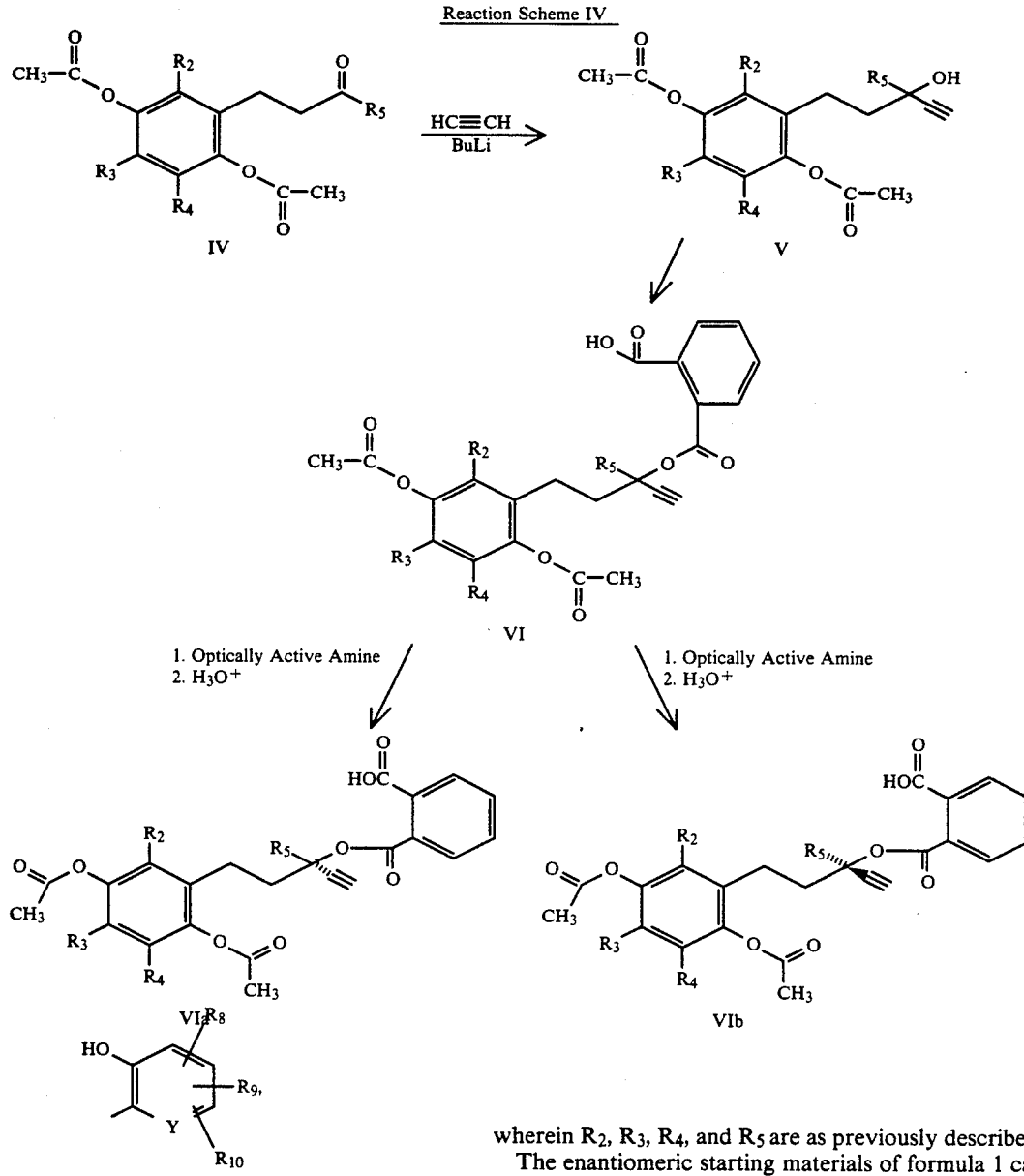

wherein Y is CH or N, and $R_1$, $R_2$, $R_3$, $R_4$, $R_5$, $R_8$, $R_9$ and $R_{10}$ are as previously discussed.

In Reaction Scheme III, a compound of formula II, which are known compounds or can be prepared according to known procedures, is converted to the corresponding compound of formula Ic by reacting with a compound of the formula $R_6'X$ in the presence of palladium catalyst, for example, bis(triphenylphosphine)palladium dichloride or diacetate and in the presence of an excess of a proton acceptor, for example, triethylamine and optionally in an inert organic solvent, for example, acetonitrile, tetrahydrofuran, dimethylformamide or the like, at a temperature in the range of from about room temperature to about 100° C.

The resulting compound of formula Ic can be separated or, in situ, undergoes conversion to the corresponding compound of formula Id by the intramolecular reaction of the hydroxy group with the triple bond to form the compound of formula Id. The compounds of formula Ic or Id can be recovered utilizing known procedures, for example, crystallization, chromatography or the like.

wherein $R_2$, $R_3$, $R_4$, and $R_5$ are as previously described.

The enantiomeric starting materials of formula 1 can be prepared as described in Reaction Schemes IV and V.

In Reaction Scheme IV, a compound of formula V can be resolved into their enantiomers by utilizing the conventional method for resolving alcohols. The preferred method is to react a compound of formula V with phthalic anhydride in the presence of a tertiary amine to form the corresponding compound of formula VI. It is noted that the compounds of formula V can be prepared by reacting a compound of formula IV, which are known compounds or can be prepared according to known procedures, with lithium acetylide. The remaining compounds of formula V can be isolated by conventional methods, e.g. crystallization, chromatography or the like. The hemiphthalates of formula VI have a free carboxy group which can be reacted with an optically active amine conventionally used for resolution. The preferred optically active amines are the enantiomeric alpha-methylbenzylamines. The diastereomeric mixture of salts formed by the reaction of the free carboxylic acid group on the ester with an optically active amine can be separated by crystallization. After separation of the diastereomeric salts they are converted to the free acids of formula VIa and VIb by treatment with aqueous acid.

or base. Salts of the compounds of formula I which have a carboxy group are prepared by the reaction with a base having a non-toxic. pharmacologically acceptable cation. In general, any base which will form a salt with a carboxylic acid and whose pharmacological properties will not cause an adverse physiological effect

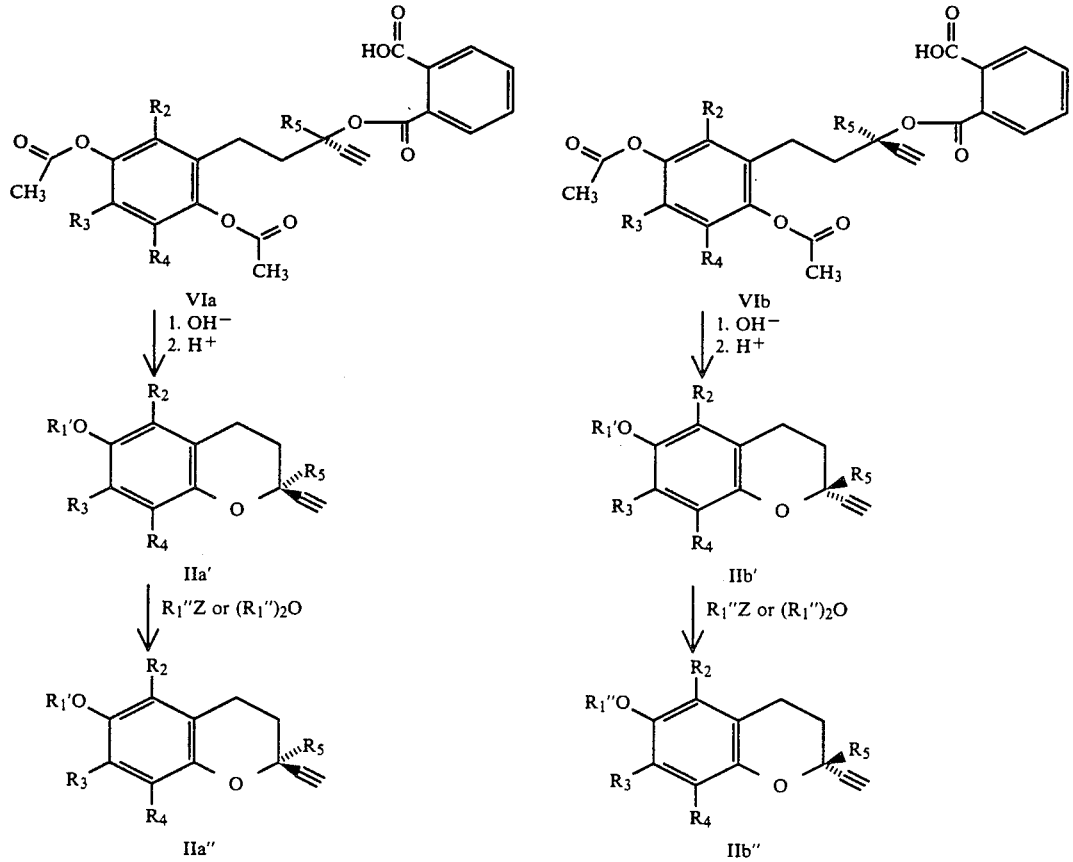

Reaction Scheme V wherein $R_1'$ is hydrogen, $R_1''$ is lower alkanoyl, Z is halogen, and $R_2$, $R_3$, $R_4$ and $R_5$ are as previously discussed.

In Reaction Scheme V, the compounds of formula VIa and VIb can be converted to the respective compound of formulas IIa' and IIb' by conventional ester hydrolysis using aqueous sodium hydroxide. The resulting intermediate alcohols are preferentially not isolated but are directly cyclized to compounds of formula IIa' and IIb' by treatment with acid in the presence of a catalytic amount of ferric ion.

The compounds of formula IIa' and IIb' can be respectively converted to the compounds of formulas IIa' and IIb' by reaction with lower alkanoyl halides of formula $R_1''Z$ or anhydrides of formula $(R_1'')_2O$. This reaction is carried out in an inert organic solvent for example, tetrahydrofuran, methylene chloride or the like in the presence of an acid acceptor, such as, pyridine, 4-dimethylamino-pyridine, triethylamine or the like.

The enantiomers of the formula IIa', IIb' IIa" and IIb" can be reacted with compounds of formula $R_6X$ to yield the corresponding enantiomeric compounds of formula I.

The invention also relates to salts of the compound of formula I, if A contains a basic or acidic functionality which lends itself for salt formation with either an acid is within the scope of this invention.

Suitable bases thus include, for example, the alkali metal and alkaline earth metal hydroxides, carbonates, and the like, for example, calcium hydroxide, sodium hydroxide, sodium carbonate, potassium carbonate and the like, ammonia, primary, secondary and tertiary amines, such as monoalkylamines, dialkylamines, trialkylamines, for example methylamine, diethylamine, triethylamine and the like, nitrogen containing heterocylic amines, for example. piperidine and the like. A salt thus produced is the functional equivalent of the corresponding compound of formula I wherein R is hydrogen and one skilled in the art will appreciate that the variety of salts embraced by the invention is limited only by the criterion that a base employed in forming the corresponding salts be both non-toxic and physiologically acceptable.

Salts of the compounds of formula I, which have a basic functionality for example, amino, pyridyl, amino lower alkyl, and the like which salts are prepared by the reaction of said amines with a non-toxic pharmacologically or pharmaceutically acceptable acid. In general, the referred to compounds of formula I form pharmaceutically acceptable addition salts with, for example, both pharmaceutically acceptable organic and inorganic acids, such as, acetic acid, succinic acid, formic acid, methanesulfonic acid p-toluenesulfonic acid, hydrochloric acid, nitric acid, phosphoric acid, sulfuric acid and the like.

The compound of formula I exhibit activity as inhibitors of 5-lipoxygenase and inhibit lipid peroxidation. They are, therefore, useful in the treatment of diseases caused or aggravated by excessive oxidative metabolism of arachidonic acid via the 5-lipoxygenase pathway and in the treatment of inflammation, arthritis, allergies, asthma and psoriasis. The compounds of formula I can also be used to prevent peroxidation of lipids and thus protect lipid membranes from oxidative stress.

IN VITRO TEST FOR $\Delta^5$-LIPOXYGENASE INHIBITORS

Compounds of formula I of the invention were tested for their effect on $\Delta^5$-lipoxygenase from rat basophilic leukemia (RBL-1) cells. Materials. RBL-1 cells (CRL 1378) were obtained from the American TYpe Culture Collection, Rockville, MD. DMEM and glutamine were purchased from Flow Labs, McLean, VA. FBS (Gibco, Grand Island, NY) was heat-inactivated for 1 hour at 56° C. Reagents for protein determinations were obtained from Biorad, Rockville Center, NY. Arachidonic acid (approx. 99%), ATP (disodium slat), BHT, dextran (clinical grade), tetrasodium EDTA, gelatin, gentamycin sulfate solution, reduced glutathione, 1 M HEPES buffer, indomethacin, NaCl, reduced NADpH, Trizma 7.2, and Trizma 8.5 were purchased from Sigma Chemical, St. Louis, MO. $CaCl_2$ dihydrate, Norit A charcoal, and citric acid monohydrate were obtained from Fisher Scientific, Pittsburgh, PA. [$^3$H]-5-HETE (specific activity 229.5 Ci/mmol) was purchased from New England Nuclear, Boston. MA. A synthetic 5-HETE standard was supplied by Dr. M. Rosenberger, Dept. of Medicinal Chemistry, Hoffmann-La Roche, Nutley, NJ; [see Corey, E.J., and Hashimoto, S. (1981) Tet. Letters, 22, 299–302 for method of preparation]. Ecoscint liquid sointillation fluid was purchased from National Diagnostics, Sommerville, NJ.

Isolation of 5-lipoxygenase. The most stable enzyme preparations were obtained from RBL-1 cells thawed from liquid $N_2$ storage, then maintained in tissue culture flasks containing DMEM supplemented with 25 mM glucose 12.5 mM HEPES, 40 mM glutamine, 50 ug/ml gentamycin sulfate, and 10% heat-inactivated FBS. Approximately 7-9 days after thawing, RBL-1 cells growing in log phase were seeded at a density of 7500 viable cells/ml in a closed 89-liter spinner flask. The cells were stirred constantly for 3–4 days at 37° C. until they reached a density greater than 500,000/ml but less than 800,00/ml. RBL-1 cells were harvested by centrifugation at 4° C. at 1500×g for 10 minutes and were washed 3 times with ice cold 0.05 M tris-HCl, pH 7.2, tetrasodium EDTA (buffer 1). The cells were washed last in 0.05 M Tris-HCl containing 14 μM indomethacin, 1 mM glutathione, 1.5 mM NaCl, and 1 mM tetrasodium EDTA (buffer 2), resuspended at a density of 5×10$^8$'/ml (approximately 10 ml) and disrupted manually at 4° C. using a 40 ml Dounce (type A pestle) homogenizer. After 5 minutes of homogenization. 95% cell lysis was confirmed by phase contrast microscopy. The broken cells were diluted 1:2 with buffer 2 and centrifuged at 12,380×g for 10 minutes at 4° C. to pellet cellular debris and granules. The 12,380×g supernatant was centrifuged at 113,000×g for 60 minutes to pellet microsomes. The high-speed supernatant (5.9±0.48 mg/ml protein) was frozen immediately in 1 ml aliquots using a dry ice/acetone bath. The isolated cytosolic fraction was stored in liquid $N_2$ for up to 8 weeks without loss of 5-LO enzyme activity.

Lipoxygenase Assay. Compounds Were dissolved at 25 mM concentration in DMSO, then diluted to final concentrations using 95% ethanol. For a typical enzyme assay, the partially purified 5-LO preparation was preincubated with drug or vehicle for 10 minutes at 30° C. The assay tubes were then transferred at a 37° C. water bath where they received arachidonic acid (8.25 μM final concentration) to initiate 5-LO activity. In addition to enzyme and substrate, each reaction tube contained: 12.5 μmoles of Tris-HCl (pH 7.2), 25 nmoles glutathione, 0.35 nmoles indomethacin and 1.25 μmoles of $CaCl_2$ and ATP to yield a total of volume of 250 μl. The enzyme reaction was terminated after 10 minutes by the addition of 75μl 0.3pM citric acid to yield pH 3.5. The samples were immediately cooled on ice and neutralized by dilution with 0.05 M Tris-HCl, pH 8.5, which contained 25 mg/1 BHT. A boiled cytosol control was placed at the end of each assay to measure non-enzymatic oxidation of arachidonic acid. The mean specific activity of the 5-LO enzyme preparation was approximately 66.16±14.39 pmol 5-HETE/min/mg protein.

Radioimmunoassay for 5-HETE. Under the assay conditions described, the 5-LO catalyzed the conversion of arachidonic acid to 5-HPETE which, as a consequence o peroxidase activity, was reduced to 5-HETE. A specific radioimmunoassay was employed to quantitate the amount (pmoles) of 5-HETE formed during the enzyme reaction. To prepare the immunogen. Dr. M. Rosenberger (Dept. of Medicinal Chemistry) converted the racemic 5-HETE lactone (Corey, E.J., and Hashimoto. S. (1981) Tet. Letters, 22, 299–302) to its hydrazine derivative. The hydrazide was conjugated to thiolated Keyhole Limpet Hemocyanin (Young, R.N., Kakushima, M., and Rokach, J. (1982) prostaglandins23, 603–613) using N-ethyl-maleimide as previously described for $LTB_4$ by (Young, R., N, Zomboni, R. and Rockach, J. 91983) prostaglandins, 26, 605–613). New Zealand White rabbits received multiple intradermal injections on their backs with 100° g conjugate emulsified in complete Freund's adjuvant. A schedule of injections reported by Salmon (Salmon, J.A. (1978) prostaglandins, 15, 383–397) was followed. After the monthly i.p. booster injections, blood was obtained from the marginal ear vein 5–7 days later and assessed for antibody titer.

Rabbit 5-HETE anti-sera was diluted 1:300 in RIA buffer (50 mM Tris-HCl plus 1.5 mM NaCl, pH 8.6, containing 0.1% gelatin) and aliquots Were mixed with standard (0.75-25 pmole 5-HETE/ml) or dilute assay samples and placed in an ice bath. [$^3$H]-5HETE (approximately 10,000–12,000 cmpm) was added to yield a total assay volume of 300 μl. After a 90 minute incubation at 25° C. 1 ml ice-cold dextran-coated charcoal was added to separate antibody-bound from unbound 5-HETE (Salmon, J.A. (1978) prostaglandins, 15, 383–397). The charcoal was sedimented at 2000×g for 10 minutes, after which 0.8 ml of supernatant was added to 10 mls Ecoscint fluid. Radioactivity (dpm) was determined after 10 minute counts using a LKB model 1219 scintillation counter (40% efficiency for [$^3$H]).

Data Analysis - Each inhibitor concentration was tested in quardruplicate. The inhibitory concentration that yielded a 50% inhibition (IC-50) of control 5-HETE formation was calculated by regression analysis of the dose-response data. Data (IC-50) for the compound of this invention this test is reported in Table. I.

MOUSE EAR EDEMA TEST (IN VIVO)

In this animal model system, the application of arachidonic acid to the ear results in the biosynthesis of the metabolic products 5-hydroperoxy-6,8,11,14-eicosatetraenoic acid (5-HETE), leukotriene $B_4$ (LTB$_4$), leukotriene $C_4$ (LTC$_4$), 12-hydroperoxy-5,8,10,14-eicosatetraenoic acid (12-HETE), and prostaglandin $E_2$ (PGE$_2$) at the site of application, followed by the influx of neutrophils into the site and the rapid development of edema within 30 to 60 minutes (See, for instance, Young, Wagner and Spries, "Tachyphylaxis in 12-O-Tetradecanoylphorbol Acetate And Arachidonic Acid-Induced Ear Edma," J. Invest. Dermatol. 80:48 (1983) and Hames, Opas and Bonney, "Arachidonic Acid Metabolites in Mouse Ear Edma" Advances in Inflammation Research. 11:57 (1986). Inhibitors of these metabolites and of their metabolic pathways also inhibit edema formation.

CD-1 male mice weighing 15 to 25 g were employed, and they were designated as follows: (1) Control Group, in which no arachidonic acid or test compound was to be applied, (2) Arachidonic Acid-Treated Group, in which no test compound was to be applied, and (3) Treated Group, in which the test compound was to be applied first, followed by the application of arachidonic acid.

In the case of the Group (3) animals, the test compound, dissolved in acetone, was applied to the dorsal surface of the right ear of the mouse with a 25-microliter pipette or, with the dose of the test compound being varied. After 0.5 hours in some cases and 4 hours in others, the arachidonic acid was topically applied in the same manner as above to the pretreated ear areas. In each case of arachidonic acid application, an amount of 0.5 mg dissolved in 25 microliters of acetone was used. After 1 hour, the mice were sacrificed by carbon dioxide inhalation. A 6mm-diameter standard biopsy punch was used to obtain a uniform tissue sample from the ear of each mouse so treated, and the tissue samples were weighted to the nearest 0.1 mg. The percent inhibition of ear edema formation was calculated as follows:

$$\frac{\text{Wt. of Arachidonic Acid Group} - \text{Wt. of Testing Group}}{\text{Wt. of Arachidonic Acid Group} - \text{Wt. of Control Group}} \times 100$$

Data for compound of this invention in this test is reported in Table 1.

IN VITRO TESTING OF ANTIPEROXIDATIVE AGENTS

The test system employs hypoxanthine-xanthine oxidase (XO)-$Fe^{3+}$·ADP as the free radical generator and purified, native rat-heart membrane phosphoglyceride in Hepes-KCl buffer, pH 7.4, as the substrate. Inhibition of superoxide-dependent, iron-promoted lipid peroxidation in the linear reaction phase (after 1 hour of reaction) is measured as the net formation of thiobarbituric acid (TBA)-reactive material. In this system, the TBA-reactive material, isolated by HPLC, is exclusively (>95%) malondialdehyde (MDA), a fragmentation end-product arising from fatty acyl hydroperoxides and cyclic endoperoxides.

a) Isolation and purification of Rat Cardiac Lipid

Conscious male Sprague-Dawley rats (~275g) maintained on a normal rodent diet were decapitated. The hearts were rapidly removed and perfused via the aorta with ice-cold 10 mM Hepes buffer, pH 7.4. The aorta and atria were removed, and the ventricular tissue was blotted and weighed (wet weight). The hearts were minced on ice with scissors and finally homogenized (100 mg tissue/ml ice-cold buffer) for 15 seconds (3×5 seconds) with a Tekmar Tissumizer at "maximal" setting. The homogenate was filtered through 4-ply cheesecloth, and homogenate lipids were extracted and purified by a modified Bligh-Dyer procedure (M.D. Marshall and M. Kates, Biochem. Biophys. Acta 260, 558 (1972). The cardiac lipids were stored in $CHCl_3$ under nitrogen at $-20°$ C.

b) Preparation of Cardiac Liposomes

Liposomes were prepared from extracted and purified, native rat heart cardiac lipid and were used as substrate for free-radical attack. Cardiac lipid (in $CHCl_3$) was placed in a glass flask and evaporated to dryness under nitrogen at room temperature; the flask was gently rotated during evaporation to yield a thin, dry lipid film. The lipid was taken up in 10 mM Hepes-0.145M KCl, pH 7.4, and was resuspended by indirect an aerobic sonification for 15 minutes at room temperature. The liposome suspension was used immediately.

c) preparation of $Fe^{3+}$-ADP Chelate

A chelate was formed in Hepes-KCl buffer between $Fe^{3+}$(1.0mM $FeCl_3$, final concentration) and ADP (10mM, final concentration) at pH 7.4 with stirring at room temperature. Chelation was allowed to proceed for 90 minutes prior to use. The chelate was prepared fresh for each days experiments to ensure iron solubility, effective chelation, and valence state.

d) Thiobarbituric Acid Reaction or Determination of Malondialdehyde Equivalents

Malondialdehyde (MDA) equivalents were measured as thiobarbituric acid (TBA)-reactive material by the following modification of published methods. The reaction mixture. prepared fresh daily, contained water: BHT (7.1 M BHT in absolute ethanol): TBA (1.5% TBA in 0.2M Tris, pH 7.0) in the volume ratio 1:1:5. To each 1.0 ml of peroxidation reaction assayed (see below), 0.35 ml reaction mixture was added. After thorough mixing, the tubes were incubated in an 80° C. shaking water bath for 30 minutes. After this time, the tubes were plunged into an ice water bath, and the reaction was immediately stopped with 0.5 ml ice-cold 91% TCA followed by 2.0 ml $CHCl_3$ After centrifugation for 30 minutes at 2000 rpm in a Sorval HL-8 rotor (4° C.), the absorbance of the washed, pink upper phase was read at 532 nm. A standard curve (0.8-40.0 nmol MDA) was run with every assay. For each curve, MDA was freshly prepared by acidification of 1,1,3,3-tetraethoxypropane with 75% TCA-2.3N HCl (0.15 ml acid mixture with 1.0 ml suitably diluted tetraethoxypropane). Computer-assisted regression analysis of the standard curve was used to quantify the molar amounts of MDA equivalents in the experimental samples.

e) Lipid peroxidation Reaction

Cardiac liposomes were subjected to superoxidedependent. iron-promoted peroxidation in glass vessels to avoid the well-known antioxidant effects of many common polymerizing agents used to fabricate plastic labware. Screening was performed in triplicate in glass 12×75 mm tubes at a final reaction volume of 1.0 ml and a reaction time of 60 minutes. Per milliliter of peroxidation reaction, the components were: Tris-HCl buffer (0.1 ml). cardiac liposomes (0.5 ml, equivalent to 125 μg phospholipid). 1 mM HX (0.1 ml). 0.1 mM $Fe^{3+}$-1.0 mM ADP chelate (0.1 ml). test substance (0.1 ml solubilized in Tris-HCl, ethanol, or DMSO) and 10 mU XOD (0.1 ml). All components are listed at their final concentrations and were prepared at the time of assay. The peroxidation reaction was started with the addition of XOD and was carried out at 37° C. in a shaking water bath. peroxidation was terminated by adding 0.15 ml ice-cold 76% TCA-2.3N HCl for each 1.0 ml of peroxidation reaction to be assayed for MDA equivalents (above). To check for possible interference by test substance, a second set of samples was run, but in these the peroxidation reaction was stopped immediately with the TCA-HCl mixture. Test substances were screened at 1.0 μM final concentration. If peroxidation were inhibited by ≧ 50%, an IC50 value was determined.

For kinetic studies, peroxidation as carried out in glass Erlenmeyer flasks. At each desired time, 1.0 ml samples, in triplicate, were withdrawn into iced tubes containing 0.15 ml 76% TCA-2.3N HCl and were then reacted with TBA (above).

f) Calculation of the Effect of a Test Substance on Lipid Peroxidations.

The effect of a test substance on cardiac lipid peroxidation during the 60 minute screening assay was taken as the ratio between the end MDA equivalents produced in the presence of the drug and the net MDA equivalents produced in its absence. The percent inhibition of lipid peroxidation was calculated by:

$$\% \text{ Inhibition of peroxidation} = 1 - \frac{\text{Drug}_{60'} - \text{Drug}_{0'}}{T_{60'} - T_{0'}} \times 100$$

$\text{Drug}_{60'}$ = MDA equivalents produced after 60 minutes with the free radical generator + test substance.

$\text{Drug}_{0'}$ = MDA equivalents produced after 0 minutes with the free radical generator + test substance.

$T_{60'}$ = Total MDA equivalents produced without test substance at 60 minutes.

$T_{0'}$ = Endogenous TBA reactivity of reaction mixture at 0 minutes.

Data for the compounds of this invention in this test is reported in Table I.

TABLE I

[Structure Ia': chroman with HO, Me substituents on aromatic ring, Me and alkynyl-$R_6$ at position with O]

| $R_6$ | EX. | ANTI-OX IC-50 μ(M) | 5-LO IC-50 (nM) | EAR EDEMA % INHIB. 1 mg |
|---|---|---|---|---|
| Phenyl | 1 | 0.65 | 40 | 45 |
| 2-HO-phenyl | 50 | 0.7 | 6 | |
| 2-HO-3-MeO-5-CHO-phenyl | 28 | >1 | 130 | |
| 2-HO-3-MeO-5-CH$_2$OH-phenyl | 29 | >1 | 130 | |
| 2-HO-3-MeO-5-CH=NOH-phenyl | 30 | >1 | 160 | |
| 2-H$_2$N-phenyl | 40 | >1 | 20 | |
| 2-F$_3$CCONH-phenyl | 44 | | 10 | |
| 3-MeO-phenyl | 22 | >1 | 170 | |
| 3-F$_3$C-phenyl | 35 | 0.8 | 190 | 15 |
| 3-AcO-4-MeO-phenyl | 20 | >1 | 24 | |
| 3-AcO-4-PhCH$_2$O-phenyl | 41 | 0.48 | 32 | 31 |
| 3-HO-4-PhCH$_2$O-phenyl | 43 | 0.37 | 24 | 31 |
| 3,4-F$_2$-phenyl | 36 | >1 | 120 | |
| 3-MeOOC-4-HO-phenyl | 23 | 0.9 | 160 | |
| 4-(3-Pyridinyl)phenyl | 24 | 0.8 | 160 | |
| 2-Thienyl, RS | 4 | 0.9 | 23 | 61 |
| 2-Thienyl, R | 5 | 0.8 | 15 | 66 |
| 2-Thienyl, S | 13 | >1 | 17 | 32 |
| 5-(2-Pyridinyl)-2-thienyl | 26 | 0.55 | 160 | |
| 3-Benzo(b)thienyl, RS | 16 | 0.56 | 1.6 | 62 |
| 3-Benzo(b)thienyl, R | 17 | | | |
| 3-Benzo(b)thienyl, S | 18 | | | |
| 2-Benzo(b)thienyl | 19 | | | |
| 2-Pyridyl | 15 | >1 | 16 | 18 |
| 3-Pyridyl | 14 | 0.6 | 40 | 20 |
| 3-Quinolinyl | 33 | 0.85 | 160 | |
| 4-Isoquinolinyl | 34 | >1 | 1000 | |
| 2-(5-Butyl)thienyl | 31 | 0.55 | 1000 | 24 |
| 4-HO-3-propyl-phenyl | 37 | >1 | | |
| 1-Naphthyl | 39 | >1 | 500 | |
| 3,4-Dihydro-4-trifluoro-acetyl-2H-1,4-benzoxazin-6-yl | 45 | | 45 | |
| 3,4-Dihydro-2H-1,4-benzoxazin-6-yl, HCl | 47 | | 18 | |

TABLE I-continued

| | | | |
|---|---|---|---|
| 4-Methyl-2H-1,4-benzoxazin-3(4H)-one-6-yl | 48 | 0.75 | 32 |

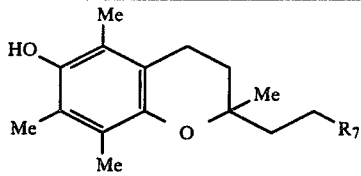

Ib'

| $R_7$ | EX. | ANTI-OX IC-50 ($\mu M$) | 5-LO IC-50 (nM) | EAR EDEMA % INHIB. 1 mg |
|---|---|---|---|---|
| Phenyl | 56 | >1 | 110 | 64 |
| 2-Thienyl | 57 | >1 | 50 | 41 |
| 2-Pyridyl | 58 | 0.7 | 60 | 31 |
| 3-Pyridyl | 59 | 0.5 | 30 | 48 |
| 3-AcO-4-MeO-phenyl | 60 | >1 | 56 | |
| 3,4-Dihydroxyphenyl | 61 | >1 | 15 | 55 |
| 3-MeO-phenyl | 62 | >1 | 120 | |
| 3-MeOOC-4-HO-phenyl | 63 | >1 | 80 | |
| 4-(3-Pyridyl)phenyl | 64 | >1 | 46 | |
| 5-(2-Pyridyl)-2-thienyl | 65 | >1 | 170 | |
| 5-Butyl-2-thienyl | 66 | >1 | 140 | |
| 3-AcO-4-HO-phenyl | 67 | | 38 | |
| 2-HO-3-MeO-5-$CH_2NH_2$-phenyl HCl | 68 | 1 | 70 | |

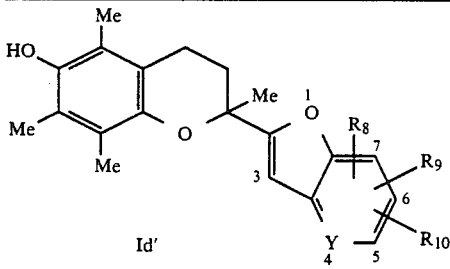

Id'

| Y | SUBSTITUENTS $R_8$, $R_9$, $R_{10}$ | EX. | ANTI-OX IC-50 ($\mu M$) | 5-LO IC-50 (nM) | EAR EDEMA % INHIB. 1 mg |
|---|---|---|---|---|---|
| N | H, H, H | 52 | 0.95 | 18 | 49 |
| N | 5-methyl, H, H | 51 | >1 | 3 | 69 |
| CH | H, H, H | 50 | 1.0 | 12 | 68 |
| CH | 5-CHO-7-MeO, H | 54 | | 1 | 40 |
| CH | 5-HOCH$_2$-7-MeO, H | 55 | 0.85 | 3 | |
| CH | 5-Acetyl-6-OH-7-propyl | 53 | 0.6 | 17 | 54 |

A compound of formula I, an enantiomer thereof or a salt thereof or a composition containing a therapeutically effective amount of a compound of formula I or a salt thereof can be administered by methods well known in the art. Thus, a compound of formula I or a salt thereof can be administered either singly or with other pharmaceutical agents, orally, parenterally, rectally, or by inhalation, for example, in the form of an aerosol, micropulverized powder or nebulized solution. For oral administration the described compound can be administered in the form of tablets, capsules, for example, in admixture with talc, starch, milk sugar or other inert ingredients, that is, pharmaceutically acceptable carriers, in the form of aqueous solutions, suspensions, elixirs or aqueous alcoholic solutions, for example, in admixture with sugar or other sweetening agents, flavoring agents, colorants, thickeners and other conventional pharmaceutical excipients, or beadlets for oral administration. For parenteral administration, the desired compound can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition. For rectal administration, the desired compound can be administered in the form of suppositories utilizing an inert carrier material cocoa butter and the like. For topical administration, the compounds of formula I can be incorporated into ointments, creams, lotions, gels, and the like. In general, the solutions, ointments and creams which are useful in accordance with this invention include formulations having absorbable, water soluble or emulsion-type bases, such as petrolatum, lanolin, polyethylene glycols, or the like.

Suitable solutions will contain the compounds of formula I dissolved in a pharmaceutically acceptable solvent, such as polyethylene glycol, or the like.

Suitable lotions include, true solutions to aqueous or hydroalcoholic formulations containing finely divided particles. Lotions can contain suspending or dispersing agents such as cellulose derivatives, for example, methyl cellulose, ethyl cellulose, or the like. Gels will typically be semi-solid preparations made by gelling a solution or suspension of a compound of formula I in a suitable hydrous or anhydrous vehicle, using a gelling agent such as carboxy polymethylene, or the like, and thereafter neutralizing it to proper consistency with an alkali metal hydroxide, for example, sodium hydroxide, and an amine, for example, polyethylenecocoamine. Topical pharmaceutical compositions containing a compound of formula I can also be formulated to include conventional ingredients such as preservatives, stabilizers, wetting agents, emulsifying agents, buffers, and the like, in conventional amounts adjusted for particular requirements and which are readily determinable by those skilled in the art.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

The compounds of formula I of the invention possesses one asymmetric carbon atom, they can thus be obtained as enantiomers or as racemic mixtures. The resolution of racemates into the optically active isomers can be carried out by known procedures. Some racemic mixtures can be precipitated as eutectics and can thereafter be separated. Chemical resolution of the starting material is, however, preferred if an enantiomer of formula I is to be prepared. By this method, diastereomeric salts are formed from the racemic mixture of a precursor of a compound of formula II, with an optically active resolving agent, for example, an optically active base, such as R-(+)-α-methylbenzylamine, which can be reacted with a carboxyl group. The formed diastereomers are separated by selective crystallization and converted to the corresponding optical isomer. Thus, the invention covers the racemates of the compounds of formula I as well as their optically active isomers (enantiomers).

The Examples which follow further illustrate the invention. All temperatures are in degrees Celsius unless otherwise stated.

EXAMPLE 1 rac-3,4-Dihydro-2,5,7,8-tetramethyl-2-(phenylethynyl)-2H-1-benzopyran-6-ol.

A mixture of 2.3 g (10 mmol) of rac-3,4-dihydro-2-ethynyl-2,5,7,8-tetramethyl-2H-1-benzopyran-6ol, 3.06 g (15 mmol) of iodobenzene, 0.39 g of triphenylphosphine. 95 mg of cuprous iodide 3 ml of triethylamine and 100 ml of acetonitrile was degassed with argon for 10 minutes. palladium acetate. 110 mg (0.5 mmol), was then added and stirring under argon was continued for 3 hours. The reaction mixture was evaporated under reduced pressure and the residue was partitioned between methylene chloride and saturated aqueous sodium bicarbonate solution. The organic phase was separated, dried over sodium sulfate and evaporated. The crude product was chromatographed over 100 g of silica gel (Merck 70-230 mesh) using methylene chloride for elution. The clean fractions were combined and evaporated and the residue was crystallized from hexane to yield 2.1 g (68 %) of rac-3,4-dihydro-2,5,7,8-tetramethyl-2-(phenylethynyl)-2H-1-benzopyran-6-ol with m.p. 109–111° C. The analytical sample was recrystallized from hexane and had m.p. 111°–113° C. Anal. Calcd. for $C_{21}H_{22}O_2$: C, 82.32; H, 7.24 Found ; C, 82.02; H, 7.30

The preparation of the starting material is described in Example 2.

EXAMPLE 2 rac-3,4-Dihydro-2-ethynyl-2,5,7,8-tetramethyl-2H-1-benzopyran-6-ol.

A solution of 50 g of rac-5-[2,5-bis(acetyloxy)- 3,4,6-trimethylphenyl]-3-methyl-1-pentyn-3-ol [H. Mayer et al. Helv. Chimica Acta, 67, 650 (1963)]in 250 ml methanol was degassed with argon. A solution of 25 g of sodium hydroxide in 30 ml of water which had also been degassed with argon was added and the mixture was heated to reflux under argon for 1.5 hours. The reaction mixture was cooled with ice-water while a mixture of 25 ml of conc. sulfuric acid in 125 ml of methanol was added. Following the addition of 0.5 g of ferric chloride trihydrate, the mixture was heated to reflux for 18 hours. It was then partitioned between methylene chloride and aqueous 10% solution of sodium carbonate. The organic layer was separated, dried over sodium sulfate and partially evaporated under reduced pressure. Hexane was added and the solution was further concentrated on the steam bath and cooled for crystallization. The crystals were collected and washed with hexane to yield 31 g (89 %) of off-white crystals with m.p. 112°–114°.

The preparation of the starting material is described in Example 3.

EXAMPLE 3

Rac-5-[2,5-Bis(acetyloxy)-3,4,6-trimethylphenyl]-3-methYl-1-pentyn-3-ol.

17.6g (0.67 mol) of acetylene gas was collected into 350 mL of dry THF (tetrahydrofuran) at -78° in a three-necked flask equipped with mechanical stirrer and dropping funnel. To this solution, under aqron, a solution of 387 mL (0.62 mol) of n-butyl lithium (1.6 M in hexane) was added dropwise at such a rate that the internal temperature was maintained at -80° to -65° C. The solution was then added dropwise, at -70° C., 64.33 g (0.21 mol) of 4-(2,5-diacetyloxy-3,4,6-trimethyl-phenylbutan-2-one in 300 of dry THF, over a period of 45 minutes. The reaction mixture was mechanically stirred at -70° C. for 1.0 h, and then the dry ice-acetone bath was removed. When the temperature of the reaction mixture reached -30° C., 500 mL of water was added dropwise very slowly, followed by addition of 50 g of ammonium chloride. The mixture was then degassed with nitrogen, and allowed to come to 25° C. After approximately 30 minutes the mixture was extracted with 2×500 mL ether. The combined organic extracts were dried over anhydrous MgSO4, filtered, and concentrated in vacuo to give 76 g of yellow oil. This material was dissolved in 25 mL of CH2Cl2, and 25 mL of ether at 30° C. Then 125 mL of hexane was added, and the solution was seeded, and refrigerated at about 4° C. for 18 h. The resulting solid was collected, washed with 100 mL of cold ether, air dried first, and again dried at 25° C. 1.0 mm for 20 h to yield 54.9 g of rac-5[2,5-bis(acetyloxy)-3,4,6-trimethylphenyl]-3-methyl-1-pentyn-3-ol as a white solid, mp 116–118° C., (softens at 96° C.). The mother liquor was concentrated in vacuo to give 19 g of the title compound as a yellow oil, which was crystallized as described above from CH2Cl2/ether/hexane (5 mL, 25 mL, and 50 mL respectively) to give a second crop of 13.3 g of title compound as a white solid for a total yield of 68.2 g (97% yield).

EXAMPLE 4 rac-3,4-Dihydro-2,5,7,8-tetramethyl-2-[(2-thienyl)ethynyl]-2H-1-benzopyran-6-ol.

A mixture of 4.6 g (20 mmol) of rac-3,4-dihydro-2-ethynyl-2,5,7,8-tetramethyl-2H-1-benzopyran-6ol, 6.3 g (30 mmol) of 2-iodothiophene, 0.8 g of triphenylphosphine, 0.19 g of cuprous iodide, 6 ml of triethylamine and 200 ml of acetonitrile was stirred and degassed with argon for 15 minutes. Palladium acetate, 220 mg, was then added and stirring under argon was continued for 4 hours. The solvent was removed under reduced pressure and the residue was partitioned between methylene chloride and saturated aqueous sodium bicarbonate soluiion. The organic phase was separated, dried and evaporated. The residue was chromato graphed over 200 g of silica gel (Merck 70-230 mesh) using methylene chloride. Crystallization of the combined clean fractions from ether/hexane yielded 3.5 g (56 %) of rac-3,4-dihydro-2,5,7,8-tetramethyl-2-[(2-thienyl) ethynyl]-2H-1-benzopyran-6ol with m.p. 112–114° C.
Anal. Calcd. for $C_{19}H_{20}O_2S$: C, 73.04; H, 6.45 Found: C, 73.10; H, 6.44.

EXAMPLE 5

(R)-3,4-Dihydro-2,5,7,8-tetramethyl-2-[(2-thienyl)ethynyl]-2H-1-benzopvran-6-ol.

This optically active compound was prepared as described in Example 4 by starting with (R)-3,4-dihydro-2-ethynyl-2,5,7,8-tetramethyl-2H-1-benzopyran-6-ol. The product was isolated by chromatography as in Example 4 and was crystallized from ether/hexane to give colorless crystals with m.p. 133–135° C. $[\alpha]_D^{25}$ 32 −36.8° (c=1.056 in MeOH). Anal Calcd. for $C_{19}H_{20}O_2S$: C, 73.04; H, 6.45 Found: C, 72.96; H, 6.52.
The optically active starting material was prepared by the resolution described in Examples 6 through 12.

EXAMPLE 6

Rac-1.2-Benzenedicarboxylic acid [3-[2,5-bis(acetyloxy)-3,4,6-trimethylphenyl]-1-ethynyl-1-methylpropyl]ester A mixture of 21.25 g (0.064 mol) of rac.-5-[2,5-bis-(acetyloxy-3,4,6-trimethylphenyl]-3-methyl 1-pentyl 3-ol), 12.12 g (0.12 mol) of triethylamine, 2.44 g (0.02 mol) of 4-dimethylaminopyridine, and 11.84 g (0.08 mol) of phthalic anhydride in 100 mL of dichloromethane was stirred at 25° C. for 3.0 h, then heated under reflux for 10 h. The reaction mixture Was cooled to 25° C. and diluted with 20 mL of diethylether. The solution was washed with 3×150 mL of 1.0 N HCl. The aqueous phase was further extracted with 2×200 mL of diethylether. The organic phases were combined and extracted with 3×100 mL of 1.0 N ammonium hydroxide. The basic aqueous extracts were combined, cooled in an ice-bath, and acidified carefully to pH 5.0 with approximately 60 mL of cold 6.0 N HCl. It was then extracted with 4×200 mL of dichloromethane. The combined extracts were dried over MgSO4. Filtration and solvent removal on a rotary evaporator (35° C., 40 mm) gave a light yellow oily residue. This material was transferred to a flask with about 100 mL of diethylether, and the solvent was evaporated as described above to give a foam, which was further dried at 25° C./0.5 mm for 18 h to yield 31 g of rac.-benzenedicarboxylic acid [3-[2,5-bis(acetyloxy)-3,4,6-trimethylphenyl]-1-ethynyl-1-methylpropyl]ester as a pale yellow foam.

EXAMPLE 7

(S)-1,2-Benzenedicarboxylic acid [3-[2,5-bis(acetyloxy)-3,4,6-trimethylphenyl-1-eIhynyl-1-methylpropyl]ester (S)-αmethylbenzenemethanamine (1:1) (salt)

To a solution of 27.00 g (0.056 mol) rac.-1,2-benzenedicarboxylic acid [3-[2,5-bis(acetyloxy)-3,4,6-trimethylphenyl]-1-ethynyl-1-methylpropyl]ester in 50 mL of 95% ethanol was added, with stirring 7.02g (0.058 mol) of (S)-(-)-α-methyl benzenemethanamine in 250 mL of diethylether. The resulting solution was stirred at 25° C. for 0.5 h, then cooled in an ice bath until crystallization occurred. It was further stirred at 0° C. for 0.5 h and the crystals were collected and air dried to give 16 g of white solid. This white solid was dissolved in 50 mL of ethanol (95%) and 150 mL of diethylether. The solution was kept at 25° C. for approximately 1.0 h and crystallization occurred. It was further stored at 0° C. for 1.0 h and the crystals were collected, dried at 25° C./0.5 mm for 24 h to yield 10.1 g of (S)-1,2-benzenedicarboxylic acid [3-[2,5-bis(acetyloxy)-3,4,6-trimethylphenyl]-1-ethynyl-1-methylpropyl]ester (S)-α-methyl benzenemethanamine (1:1) (salt) as a white solid (30% yield from racemic starting materials), m.p. 162°–165°.
The mother liquor from this crystallization of the white solid was used in Example 8.

EXAMPLE 8

(R)-1,2-Benzenedicarboxylic acid [3-[2,5-bis(acetyloxy)-3,4,6-trimethylphenyl]-1-ethynyl-1-methylpropyl]ester (R)-α-methylbenzenemethanamine (1:1) (salt)

The recovered mother liquor from Example 7 was evaporated to give an oily residue which was taken into 100 mL of diethylether and treated with 100 mL of 1.0 N HCl. The mixture was stirred vigorously for 0.5 h. The ether layer was separated and further washed with 2×100 mL =200 mL of 1.0 N HCl, and 100 mL of water. The aqueous phase was back extracted with 100 mL of diethylether. The ether extracts were combined, dried over MgSO4, and filtered. To this etheral filtrate was added 50 mL of 95% ethanol, followed by 5.2 g (0.043 mol) of (R)-(+)-α-methylbenzylamine. The solution was stirred at 0° C. for 1.0 h and the resulting crystalline substance was collected by filtration to give approximately 18 g of white solid. It was recrystallized from 50 mL of ethanol and 150 of diethylether (as described in Example 7) to give 11.04 g of (R)-1,2-benzenedicarboxylic acid [3-[2,5-bis(acetyloxy)-3,4,6-trimethylphenyl]-1-ethynyl-1-methylpropyl]ester (R)-α-methyl benzenemethanamine (1:1) (salt) as a white solid (32.8% yield); mp 163°-166° C., $[\alpha]_D^{25} = +9.6°$ (c=1.03, $C_2H_5OH$).

EXAMPLE 9

(S)-(+)-1,2-Benzenedicarboxylic acid [3-[2,5-bis(acetyloxy)-3,4,6--trimethylphenyl]-1-ethynyl-1-methylpropyl]ester A mixture of (S)-1,2-benzenedicarboxylic acid [3-[2,5-bis(acetyloxy)3,4,6-trimethylphenyl]-1-ethynyl-1-methylpropyl-9 ester(S)-α-methyl benzenemethanamine (1:1) (salt) (110 g, 0.17 mol), 400 mL of 1.0 N HCl, and 40 mL of $CH_2Cl_2$-ether (1:9) was stirred vigorously for 1.0 h at 25° C. It was then extracted with ether (2×200 mL). The ether extracts were combined, washed with 1.0 N HCl (200 mL), water (200 mL), and dried over anhydrous $MgSO_4$. Evaporation of ether in vacuo gave a solid which was further dried at 25° C./0.5 mm for 16 h to afford 80.5g of (S)-(+)-1,2-benzenedicarboxylic acid [3-[2,5-bis(acetyloxy)-3,4,6-trimethylphenyl]-1-ethynyl-1-methylpropyl]ester as a white foam: $[\alpha]_D^{25} = +15.95°$ (c=0.96, ethanol).

EXAMPLE 10

(R)-(-)-1,2-Benzenedicarboxylic acid [3-[2-bis(acetyloxy)-3,4,6-trimethylphenyl]-1-ethynyl-1-methylpropyl]ester The title compound was prepared from (R)-1,2-benzenedicarboxylic acid [3-[2,5-bis(acetyloxy)-3,4,6-trimethylphenyl]-1-ethynyl-1-methylpropyl]ester(R)-α-methyl benzenemethanamine (1:1) (salt) by the procedure described in Example 9. The product was a white foam: $[\alpha]_D^{25} = -15.98°$ (ethanol).

EXAMPLE 11

(S)-(+)-3,4-Dihydro-2-ethynyl-2,5,7,8-tetramethyl-2H-1-benzopyran-6-ol.

48 0 g (0.1 M) of (S)-1,2-benzenedicarboxylic acid [3-[2,5-bis(acetyloxy)-3,4,6-trimethylphenyl]-1-ethynyl-1methylpropyl]ester was dissolved in 250 mL of methyl alcohol and degassed with argon. To this solution, 150 mL (0.9 M) of 6N NaOH was added dropwise. It was then refluxed for 1.0 h, cooled to ~4° C., and acidified to pH 1.5 with 150 mL of 5.6 N $H_2SO_4$. 200 mL of MeOH and 0.2 g ferric chloride trihydrate were added. The reaction mixture was heated under reflux for 18 h. It was cooled to 25° C. and 500 mL of water was added. The mixture was extracted with 3×300 mL diethyl ether. The ether extracts were combined, washed successively with 3×300 mL saturated sodium bicarbonate solution, 3×300 mL 1 N HCl, 3×300 mL water, and dried over anhydrous $MgSO_4$. After filtration, the ether solution was further passed through a short plug of 500 g of forisil which was further washed with 500 mL ether. Evaporation of the ether in vacuo gave 23 g of orange-tan solid. Crystallization of this material from toluene/hexane (1:5) gave 15.62 g of (S)-(+)-3,4-dihydro-2-ethynyl-2,5,7,8-tetramethyl-2H-1-benzopyran-6-ol as needles: mp 109°-114° C., $[\alpha]_D^{25} = +53.46°$ (c=0.997, $CHCl_3$). A second crop of 2.94 g of this compound was also obtained, mp 108°-117° C., $[\alpha]_D^{25} = +53.63°$ (c=0.985, $HCl_3$) A total yield (80.5%) 18.56 g of product was obtained.

EXAMPLE 12

(R)-(+)-3,4-Dihydro-2-ethynyl-2,5,7,8-tetramethyl-2H-1-benzopyran-6-ol.

Based on the procedure described in Example 11, 18.1g of (R)-(+)-3,4-dihydro-2-ethynyl-2,5,7,8-tetramethyl-2H-1-benzopyran-6-ol was prepared in a 78% yield from 48 g of (R)-1,2-benzenedicarboxylic acid [3-[2,5-bis(acetyloxy)-3,4,6-trimethylphenyl]-1-ethynyl-1-methylpropyl]ester. The product was obtained as a white needles: mp 109°-114° C., $[\alpha]_D^{25} = +55.72°$ (c+1.001, $CHCl_3$).

EXAMPLE 13

(S)-3,4-Dihydro-2,5,7,8-tetramethyl-2-[(2-thienyl)ethynyl]-2H-1-benzopyran-6-ol.

This enantiomer was obtained as described in Example 4 by reacting the (S)-3,4-dihydro-2-ethynyl-2,5,7,8-tetramethyl-2H-1-benzopyran-6-ol from Example 11 with 2-iodothiophene. It was isolated by chromatography as above and was crystallized from ether/hexane to yield colorless crystals with m.p. 131°-134° C. $[\alpha]_D^{25} = +34.9°$ (c=1.14in MeOH).

Anal. Calcd. for $C_{19}H_{20}O_2S$: C, 73.04; H, 6.45 Found: C, 73.08; H, 6.51

EXAMPLE 14 rac-3,4-Dihydro-2,5,7,8-tetramethyl-2-[(3-pyridinyl)ethynyl]-2H-1-benzopyran-6-ol.

Rac-3,4-dihydro-2-ethynyl-2,5,7,8-tetramethyl-2H-1-benzopyran-6-ol, 4,6g, was reacted as described in Example 4 with 4.74 g of 3-bromopyridine. The reaction time was extended to 18 hours. The product was isolated by chromatography over 150 g of silica gel using 10 % (v/v) of ethyl acetate in methylene chloride for elution. Crystallization of the combined clean fractions from ethyl acetate/hexane gave off-white crystals with m.p. 172°-175° C. The analytical sample was recrystallized from tetrahydrofuran/hexane and had m.p. 175-178° C.

Anal. Calcd. for $C_{20}H_{21}NO_2$: C, 78.15; H, 6.89; N, 4.56 Found: C., 77.49; H, 7.23; N, 4.45

EXAMPLE 15 rac-3,4-Dihydro-2,5,7,8-tetramethyl1-2-[(2-pyridinyl)ethynyl]-2H-1-benzopyran-6-ol.

This compound was prepared by reacting rac-3,4-dihydro 2-ethynyl-2,5,7,8-tetramethyl-2H-1-benzopyran-6-ol with 2-bromopyridine as described in Example 14. The compound was isolated by chromatography as in Example 14 and was crystallized from ethyl acetate to give colorless crystals with m.p. 179°-181° C.

Calcd. for $C_{20}H_{21}NO_2$: C, 78.15; H, 6.89; N, 4.56 Found: C, 77.76; H, 6.97; N, 4.43

EXAMPle 16 rac-[2-(Benzo[b]thiophen-3-yl)ethynyl]-3.4-dihydro-2,5,7,8-tetramethyl-2H-1-benzopyran-2H-1-benzopyran-6-ol.

A mixture of 4.6 g (20 mmol) of rac-3,4-dihydro-2-ethynyl-2,5,7,8-tetramethyl-2H-1-benzopyran-6-ol, 6.4 g (30 mmol) of 3-bromobenzo[b]thiophene 0.4 g of triphenylphosphine, 95 mg of cuprous iodide, 6 ml of triethylamine and 150 ml of acetonitrile was degassed with argon for 15 minutes. Palladium acetate, 110 mg, was then added and stirring at room-temperature was continued for 4 days. The solvent was evaporated under reduced pressure and the residue was partitioned between methylene chloride and saturated aqueous sodium bicarbonate solution. The organic layer was separated, dried over sodium sulfate and evaporated. The residue was chromatographed over 200 g of silica gel using methylene chloride/hexane 1:1(v/v) for elution. Crystallization of the combined clean fractions from ether/hexane yielded 3.3 g (45.5%) of colorless crystals with m.p. 123°–124° C. A lower melting modification with m.p. 88°–91° C. was also observed.

Anal. Calcd. for $C_{23}H_{22}O_2S$: C, 76.21; H, 6.12 Found C, 76.01; H, 6.21

EXAMPLE 17

S(+)-[2-(Benzo[b]thiophen-3-yl)ethynyl]-3,4-dihydro-2,5,7,8-tetramethyl-2H-1-benzopyran-6-ol.

This enantiomer was prepared as described above by using S(+)-3,4-dihydro-2-ethynyl-2,5,7,8-tetramethyl-2H 1-benzopyran-6-ol from Example 11 as the starting material. The product was isolated as described in Example 16 by chromatography and was crystallized from methanol/water to give colorless crystals with m.p. 58°–61° and $[\alpha]_D^{25}$ 32 +31.58° (c=1.045 in MeOH).

Anal. Calcd. for $C_{23}H_{22}O_2S$. 0.33 $H_2O$: C. 74.96; H, 6.20 Found: C. 75.26; H, 5.91

EXAMPLE 18

R(-)-2-(Benzo[b]thiophen-3-yl)ethynyl]-3.4-dihydro-2,5,7,8-tetramethyl-2H-1-benzopyran-6-ol.

This optical isomer of the compound described in Example 17 was obtained by reacting R(-)-3,4-dihydro-2-ethynyl-2,5,7,8-tetramethyl-2H-1-benzopyran-6-ol from Example 12 with 3-bromobenzo[b]thiophene under the conditions described in Example 16. The product was isolated in the same fashion and was crystallized from methanol/water to leave colorless crystals with m p. 58°–61° and $[\alpha]_D^{25}$ = −30.11° (C=1.002 in MeOH).

Anal. Calcd. for $C_{23}H_{22}O_2S$. 0.33 $H_2O$: C. 74.96; H, 6.20 Found: C, 74.51; H, 5.88

EXAMPLE 19 rac-2-(Benzo[b]thiophen-2-yl)ethynyl]-3,4-dihydro-2,5,7,8-tetramethyl-2H-1-benzopyran-6-ol.

Reaction of rac-3,4-dihydro-2-ethynyl-2,5,7,8-tetramethyl-2H-1-benzopyran-6-ol with 2-bromobenzo[b]thiophene under the conditions described in example 16 gave after chromatographic isolation and crystallization from ether/hexane colorless crystals with m.p. 120°–123° C.

Anal Calcd. for $C_{23}H_{22}O_2S$: C, 76.21; H, 6.12 Found: C. 76.00; H, 5.77

EXAMPle 20 rac-2-[(3-Acetyloxy-4-methoxyphenyl)ethynyl]-3,4-dihydro-2,5,7,8-tetramethyl-2H-1-benzopyran-6-ol.

rac-3,4-Dihydro-2-ethynyl-2,5,7,8-tetramethyl-2H-1-benzopyran-6-ol. 1.15 g (5 mmol), Was reacted with 1.5 g (5.12 mmol) of (5-iodo-2-methoxyphenyl)acetate under the conditions described in Example 4. The product was isolated by chromatography over 70 g of silica gel using 5% (v/v) of ethyl acetate in methylene chloride for elution. The clean fractions were combined and evaporated and the residue was crystallized from ethyl acetate/ether/hexane to give 1.4 g (70%) of off-white crystals with m.p. 142°–144° C.

Anal. Calcd. for $C_{24}H_{26}O_5$: C, 73.08; H, 6.64 Found: C, 73.02; H, 6.73

The preparation of the starting material is described in Example 21.

EXAMPLE 21

(5-Iodo-2-methoxyphenyl)acetate

A mixture of 12.5 g (0.1 mol) of 2-methoxyphenol, 20 ml of pyridine and 25 ml of acetic anhydride was allowed to sit at room temperature over night. The reagents were evaporated under reduced pressure, at the end azeotropically with toluene. The residue was dissolved in 100 ml of glacial acetic acid. Iodine monochloride, 10 ml or 31 g, was added in portions over 15 minutes. Following the addition, the mixture was stirred for 2 hours at room temperature and then diluted with water and treated with excess sodium sulfite. The product was extracted with methylene chloride and the extracts were washed with sodium sulfite solution, dried and evaporated. The residue was crystallized from ether/hexane with cooling in ice-water. Recrystallization from the same solvents gave colorless crystals with m.p. 89°–90°.

Anal. Calcd. for C : $C_9H_9IO_3$: C, 37.01; H, 3.11 Found: C, 36.64; H. 2.98

EXAMPLE 22 rac-3,4-Dihydro-2-(3-methoxyphenyl)ethynyl)-2,5,7,8-tetra-methyl-2H-1-benzopyran-6-ol.

Reaction of 1.15 g (5 mmol) of rac-3,4-dihydro-2-ethynyl-2,5,7,8-tetramethyl-2H-1-benzopyran-6-ol and 1.5 ml (12.5 mmol of 3-methoxy-iodobenzene as described in Example 4 yielded after isolation by chromatography over 60 g of silica gel with methylene chloride and crystallization from ether/hexane 1.05 g (62.5%) of colorless crystals with m.p. 108°–112° C.

Anal. Calcd. for $C_{22}H_{24}O_3$: C, 78.54; H. 7.19 Found: C. 78.65; H. 7.29

EXAMPLE 23 rac-5-(3,4-Dihydro-6-hydroxy-2,5,7,8-tetramethyl-2H-1-benzopyran-2-yl)ethynyl]-2-hydroxybenzoic acid methyl ester.

rac-5-[(3,4-dihydro-6-hydroxy-2,5,7,8-tetramethyl-2H-1-benzopyran-2-yl)ethynyl]-2-hydroxybenzoic acid methyl ester was prepared by reacting rac-3,4-dihydro-2-ethynyl 2,5,7,8-tetramethyl-2H-1-benzopyran-6 ol with 2 hydroxy-5-iodobenzoic acid methyl ester [M. Covello. Chim. Ther. 2, 73 (1967)]as described in Example 4. The compound was isolated by chromatography over silica gel using methylene chloride and was crystallized from ethyl acetate/hexane to yield colorless crystals with m.p. 151°–153° C.

Anal. Calcd. for $C_{23}H_{24}O_5$: C, 72.61; H, 6.36 Found: C. 72.34; H. 6.45

EXAMPLE 24 rac-3,4-Dihydro-2,5,7,8-tetramethyl-2-{[4-(3-pyridinyl)-phenyl]ethynyl}-2H-1-benzopyran-6-ol.

A mixture of 1.15 g of rac-3.4-dihydro-2-ethynyl-2,5,7,8-tetramethyl-2H-1-benzopyran-6-ol, 1.14 g (4mmol) of 3-(4iodophenyl)pyridine, 0.2 g of triphenylphosphine, 50 mg of cuprous iodide, 1.5 ml of triethylamine and 20 ml of acetonitrile was degassed with argon for 10 minutes. Palladium acetate, 75 mg. was then added and stirring was continued for 3 hours. The reaction mixture was partitioned between methylene chloride and water. The organic layer was dried and evaporated. The residue was crystallized from ethyl acetate and recrystallized from methanol/ethyl acetate to give colorless crystals with m.p. 190°-192° C.

Anal. Calcd. for $C_{26}H_{25}NO_2$: C, 81.43; H, 6.57; N, 3.65 Found: C, 81.71; H, 6.63; N, 3.59

The starting material was obtained as shown in Example 25.

EXAMPLE 25

3-(4-Iodophenyl)pyridine.

A mixture of 1.7 g (10 mmol) of 3-(4-aminophenyl)pyridine [F. S. Tanaka et al.. J. Agric. Food Chem. 30, 957 (1982)], 17 ml of glacial acetic acid and 1.5 ml of trifluoroacetic acid was cooled in ice-water. Sodium nitrite. 0.8 g (11.4 mmol) was added in portions. After stirring for 15 minutes in ice-water and 15 minutes without cooling, 5 g of sodium iodide and 3 g of sodium acetate was added slowly with water cooling. The reaction mixture was diluted with 30 ml of water and stirred for 30 minutes. It was then partitioned between methylene chloride and 10% aqueous sodium carbonate solution. The organic phase was dried and evaporated and the residue was chromatographed over 20 g of silica gel using 10% (V/V) of ethyl acetate in methylene chloride. Crystallization from hexane yielded off-white crystals with m.p. 112°-115°.

Anal. Calcd. for $C_{11}H_8IN$: C, 47.00; H, 2.87; N, 4.98 Found C. 46.92; H, 2.72; N, 4.88.

EXAMPLE 26 rac-3,4-Dihydro-2,5,7,8-tetramethyl-2-{[5-(2-pyridinyl)-2-thienyl]ethynyl}-2H-1-benzopyran-6-ol.

A mixture of 2.3 g of rac-3,4-dihydro-2-ethynyl-2,5,7,8-tetramethyl-2H-1-benzopyran-6-ol, 3.6 g (15 mmol) of 2-(5-bromo-2-thienyl)pyridine, 0.39 g of triphenylphosphine, 95 mg of cuprous iodide. 3 ml of triethylamine and 100 ml of acetnitrile was degassed with argon for 10 minutes. Palladium acetate, 110 mg. was then added and the mixture was stirred at room temperature for 18 hrs. After evaporation under reduced pressure, the residue was partitioned between methylene chloride and water. The organic layer was dried and evaporated and the residue was chromatographed over 140 g of silica gel using 5% of ethyl acetate in methylene chloride. The combined clean fractions were evaporated and the residue was crystallized from ether/hexane to yield 2 g of colorless crystals with m.p. 159°-162° . The analytical sample was recrystallized from ethanol and had m.p. 160°-162°.

Anal. Calcd. for $C_{24}H_{23}NO_2S$: C, 74.01; H, 5.95; N, 3.60 Found: C, 73.88; H, 6.00; N, 3.46

The preparation of the arylhalide component is described below in Example 27.

EXAMPLE 27

2-(5-Brom.-2-tohienyl)pyridine.

Bromine. 16 g (0.1 mol), was added to a solution of 8.05g (0.05 mol) of 2-(2-thienyl)pyridine in 250 ml of methylene chloride. After stirring for 10 minutes, the reaction mixture was washed with 10% aqueous sodium carbonate solution, dried and evaporated. Crystallization from ethanol gave 9.5g of the title compound with m.p. 85°-87°.

Anal. Calcd. for $C_9H_6BrNS$: C, 45.01; H, 2.51; N, 5.83 Found: C, 45.07; H, 2.37; N, 5.92.

EXAMPLE 28 rac-3-[(3,4-Dihydro-6-hydroxy-2,5,7,8-tetramethyl-2H-1-benzopyran-2-yl)ethynyl]-4-hydroxy-5-methoxybenzaldehyde.

Rac-3,4-dihydro-2-ethynyl-2,5,7,8-tetramethyl-2H-1-benzopyran-6-ol. 2.3 g was reacted with 4.17 g (15 mmol) of 5-iodovanilline as described in example 1, but extending the reaction time to 4.5 hours. After the usual workup, the residue was chromatographed over 150 g of silica gel using 10% (V/V) of ethyl acetate in methylene chloride. Crystallization from ether/hexane and recrystallization from ethyl acetate/hexane yielded colorless crystals with m.p. 158°-160°.

Anal Calcd. for $C_{23}H_{24}O_5$: C, 72.61; H, 6.36 Found: C, 72.60; H, 6.42

EXAMPLE 29 rac-3-[(3,4-Dihydro-6-hydroxy-2,5,7,8-tetramethyl-2H-1-benzopyran-2-yl)ethynyl]-4-hydroxy-5-methoxybenzenemethanol.

This compound was obtained by reacting rac-3,4-dihydro-2-ethynyl-2,5,7,8-tetramethyl-2H-1-benzopyran-6-ol with 3-iodo-4-hydroxy-5-methoxybenzenemethanol [P. Claus et al. Monatsh. Chem. 103, 1178 (1972)] under the conditions described in Example 1. The product was isolated by chromatography over silica gel using 30 % (V/V) of ethyl acetate in methylene chloride. Crystallization from ether/ hexane yielded colorless crystals with m.p. 160°-163°.

Anal. Calcd. for $C_{23}H_{26}O_5$: C, 72.23; H, 6.85 Found: C, 72.05; H, 7.13

EXAMPLE 30 rac-3-[(3,4-Dihydro-6-hydroxy-2,5,7,8-tetramethyl-2H-1-benzopyran-2yl)ethynyl]-4-hydroxy-5-methoxybenzaldehydeoxime.

This compound was prepared by reacting rac-3,4-dihydro-2-ethynyl-2,5,7,8-tetramethyl-2H-1-benzopyran-6 -ol with 3-iodo-4 hydroxy-5-methoxybenzaldehyde oxime under the conditions described in Example 1. The reaction time was 4 hours. The product was crystallized from ethyl acetate/ether after the usual workup and was recrystallized twice from methanol/ethyl acetate to give colorless crystals with m.p. 210°-213°.

Anal. Calcd. for $C_{23}H_{25}NO_5$: C, 69.86; H, 6.37; N, 3.54 Found: C, 69.89; H, 6.52; N, 3.57

EXAMPLE 31 rac-2-[(5-Butyl-2-thienyl)ethynyl]-3,4-dihydro-2,5,7,8-tetramethyl-2H-1-benzopyran-6-ol.

rac-3,4-Dihydro-2-ethynyl-2,5,7,8-tetramethyl-2H-1-benzopyran-6-ol. 2,3 g (10 mmol) was reacted with 2.4 g (11 mmol) of 2-bromo-5-butylthiophene under the conditions described in Example 15. Chromatography of the crude product over 100 g of silica gel and crystallization from petroleum ether yielded colorless crystals with m.p. 80°-82°.

Anal. Calcd. for $C_{23}H_{28}O_2S$: C, 74.96; H, 7.66 Found: C, 74.87; H, 7.62

The preparation of the starting material is described in Example 32.

EXAMPLE 32

2-Bromo-5-butylthiophene

Bromine, 5 ml (15.63 g or 0.0977 mol), was added to a solution of 15.2 g (0.108 mol) of 2-butylthiophene in 400 ml of chloroform. Following the addition, the mixture was stirred for 10 minutes at room temperature and was then washed with 10% aqueous sodium carbonate solution. The organic layer was separated, dried and evaporated and the remaining oil was distilled under high vacuum to yield a colorless oil. Nmr ($CDCl_3$): 0.89 ppm (t, 3, J=7.5 Hz, $CH_3$). 1.2-1.7 (m, 4, $CH_2CH_2$), 2.7 (t, 2, J=7.5 Hz, $CH_2$). 6.47 (d, 1, J=4 Hz. C4-H), 6.78 (d, 1, J=4 Hz. C3-H).

EXAMPLE, 33 rac-3,4-Dihydro-2,5,7,8-tetramethyl-2-(3-quinolinylethynyl)-2H-1-benzopyran-6-ol.

This compound was obtained by reacting rac-3,4-dihydro-2-ethynyl-2,5,7,8-tetramethyl-2H-1-benzopyran-6-ol, 2.3 g (10 mmol), with 3.12 g (15 mmol) of 3-bromoquinoline as described in Example 15. The product was crystallized from methylene chloride/ethanol and was recrystallized from ethyl acetate to yield tan crystals with m.p. 199°-203°.

Anal. Calcd. for $C_{24}H_{23}NO_2$: C, 80.64; H, 6.49; N, 3.92 Found: C, 80.58; H, 6.60; N, 3.95

EXAMPLE 34 rac-3,4-Dihydro-2-[(4-isoquinolinyl)ethynyl]-2,5,7,8-tetramethyl-2H-1-benzopyran-6-ol.

rac-3,4-dihydro-2-[(4-isoquinolinyl)ethynyl]-2,5,7,8-tetramethyl-2H-1-benzopyran-6-ol was obtained by substituting 3-bromoquinoline with 4-bromoisoquinoline in the above Example. The product was crystallized from methylene chloride/ethanol and was further purified by chromatography over the 30 fold amount of silica gel using 5 % (V/V) of ethanol in methylene chloride. The analytical sample was recrystallized from toluene and had m.p. 227°-230°.

Anal. Calcd. for $C_{24}H_{23}NO_2$: C, 80.64; H, 6.49; N, 3.92 Found: C, 80.64; H, 6.45; N, 3.88

EXAMPLE 35 rac-2-{[3-(Trifluoromethyl)phenyl]ethynyl-3,4-dihydro-2,5,7,8-tetramethyl-2H-1-benzopyran-6-ol.

This compound was similarly prepared by reacting rac-3,4-dihydro-2-ethynyl-2,5,7,8-tetramethyl-2H-1-benzopyran-6-ol with 3-trifluoromethylbromobenzene as described in Example 26. The product was isolated by chromatography over 50 fold amount of silica gel using methylene chloride for elution. Crystallization of the combined clean fractions from petroleum ether gave colorless crystals with m.p. 81°-83°.

Anal. Calcd. for $C_{22}H_{21}F_3O_2$: C, 70.58; H, 5.65 Found: C, 70.50: H, 5.81

EXAMPLE 36 rac-2-[(3,4-Difluorophenyl)ethynyl]-3,4-dihydro-2,5,7,8-tetramethyl-2H-1-benzopyran-6-ol.

Reaction of rac-3,4-dihydro-2-ethynyl-2,5,7,8-tetramethyl-2H-1-benzopyran-6-ol with 1-bromo-3,4-difluorobenzene under the conditions described in Example 26 and extending the reaction time to 42 hours gave after chromatographic isolation (40 fold amount of silica gel using methylene chloride) and crystallization from petroleum ether colorless crystals of the title compound with m.p. 109°-112°.

Anal. Calcd. for $C_{21}H_{20}F_2O_2$: C, 73.67; H, 5.89 Found: C, 73.78; H, 6.21

EXAMPLE 37 rac-3,4-Dihydro-2-[(4-hydroxy-3-propylphenyl)ethynyl]-2,5,7,8-tetramethyl-2H-1-benzopyran-6-ol.

This compound was obtained by reacting rac-3,4-dihydro-2-ethynyl-2,5,7,8-tetramethyl-2H-1-6ol with 4-iodo-2-propylphenol under the conditions described in Example 1. The product was isolated by chromatography over the 40 fold amount of silica gel using 10% (V/V) of ethyl acetate in methylene chloride. It was crystallized from ether/hexane to give off-white crystals with m.p. 154°-156°.

Anal. Calcd. for $C_{24}H_{28}O_3$: C, 79.09; H, 7.74 Found: C, 78.87; H, 7.68

The starting iodo compound was obtained as shown in Example 38.

EXAMPLE 38

4-Iodo-2-propylphenol.

A mixture of 6.8 g (50 mmol) of 2-propylphenol. 8.25 g (55 mmol) of sodium iodide. 175 ml of acetonitrile and 40 ml of water was cooled on ice. t-Butylhypochlorite, 6 g or 6.56 ml (55 mmol), was added slowly at 0°. After stirring for 10 minutes at 0°, 500 ml of ethyl acetate was added and the mixture was washed with 5% aqueous solution of sodium thiosulfate. The organic layer was dried and evaporated and the residue was chromatographed over 150 g of silica gel using methylene chloride/hexane 3:2. The more polar monoiodinated product was crystallized from petroleum ether to give colorless crystals with m.p. 54°-56°.

Anal. Calcd. for $C_9H_{11}IO$: C, 41.24; H, 4.23 Found: C, 41.36; H, 4.29

EXAMPLE 39 rac-3,4-Dihydro-2,5,7,8-tetramethyl-2-(1-naphthyl)ethynyl-2H-1-benzopyran-6-ol.

rac-3,4-dihydro-2,5,7,8-tetramethyl-2-[(1-naphthyl)ethynyl]-2H-1-benzopyran-6-ol was prepared by coupling rac-3,4-dihydro-2-ethynyl-2,5,7,8-tetramethyl-2H-1-benzopyran6-ol with 1-iodonaphthalene under the conditions described in Example 1. It was isolated by chromatography over 40 fold amount of silica gel using methylene chloride. The combined clean fractions were crystallized from hexane and recrystallized from petroleum ether to give colorless crystals with m.p. 127°-128°.

Anal. Calcd. for $C_{25}H_{24}O_2$: C, 84.24; H, 6.79 Found: C, 84.15; H, 6.83

EXAMPLE 40 rac-2-[(2-Aminophenyl)ethynyl]-3,4-dihydro-2,5,7,8-tetramethyl-2H-1-benzopyran-6-ol.

This compound was obtained by reacting rac-3,4-dihydro-2-ethynyl-2,5,7,8-tetramethyl-2H-1-benzopyran-6-ol with 2-iodoaniline under the conditions described in Example 26. The product was isolated by chromatography over the 40 fold amount of silica gel using methylene chloride. Crystallization from ether/hexane and recrystallization from cyclohexane gave pale yellow crystals with m.p. 110°–112°.

Anal. Calcd. for $C_{21}H_{23}NO_2$: C, 78.47; H, 7.21; N, 4.36 Found: C, 78.41; H, 7.23; N, 4.20

EXAMPLE 41 rac-2-{[3-Acetyloxy-4-(phenylmethoxy)phenyl]ethynyl}-3,4-dihydro-2,5,7,8-tetramethyl-2H-1-benzopyran-6-ol.

This compound was obtained by coupling rac-3,4-dihydro-2-ethynyl-2,5,7,8-tetramethyl-2H-1-benzopyran-6-ol with 5-iodo-2-(phenylmethoxy)phenyl acetate under the conditions described in Example 26. The crude product was chromatographed over the 50 fold amount of silica gel using methylene chloride. The combined fractions were evaporated and the residue was crystallized from methanol after treatment with charcoal and was recrystallized from ether/ hexane for analysis to give colorless crystals with m.p. 117°–120°.

Anal. Calcd. for $C_{30}H_{30}O_5$: C, 76.57, H, 6.43 Found: C, 76.13, H, 6.52

The starting iodo compound was prepared as described in Example 42.

EXAMPLE 42

5-Iodo-2-(phenylmethoxy)phenol acetate.

A mixture of 8 g of 2-(phenylmethoxy)phenol. 20 ml of pyridine and 30 ml of acetic anhydride was allowed to sit at room temperature over night. The reagents were evaporated under reduced pressure, at the end azeotropically with xylene and then with carbon tetrachloride. The residue. 7.5 g, was dissolved in 80 ml of acetic acid and the solution was cooled in ice-water. Iodine monochloride. 19 g, was added and the mixture was stirred for 30 minutes. It was then poured onto ice-water, treated with sodium sulfite and extracted with methylene chloride. The extracts were washed with 10% aqueous sodium carbonate solution, dried and evaporated. The residue was crystallized from hexane and recrystallized from methanol to yield colorless crystals with m.p. 71°–73°.

Anal. Calcd. for $C_{15}H_{13}IO_3$: C, 48.94; H, 3.56 Found: C, 49.00; H, 3,42

EXAMPLE 43 rac-3,4-Dihydro-2-{[3-hydroxy-4-(phenylmethoxY)phenyl]-ethynyl}-2,5,7,8-tetramethyl-2H-1-benzopyran-6-ol.

Sodium hydroxide, 0.12 g (3 mmol). was added to a solution of 0.47 g (1 mmol) of rac-2-{[3-acetyloxy.4-(phenylmethoxy)phenyl]ethynyl}-3,4-dihydro-2,5,7,8-tetramethyl-2H-1-benzopyran-6ol in 10 ml of methanol. The mixture was stirred under argon for 1.5 hours and was then acidified with glacial acetic acid and partitioned between methylene chloride and saturated aqueous sodium bicarbonate solution. The methylene chloride layer was separated, dried and passed over a pad of silica gel. The filtrate was evaporated and the residue was crystallized from ether/ hexane to give colorless crystals with m.p. 103°–106°.

Anal. Calcd. for $C_{28}H_{28}O_4$: C, 78.48; H, 6.59 Found C, 78.21; H, 6.73

EXAMPLE 44 rac-2,2,2-Trifluoro-N-{2-[(3,4-dihydro-6-hydroxy-2,5,7,8-tetramethyl-2H-1-benzopyran-2-yl)ethynyl]phenyl}acetamide.

Trifluoroacetic acid anhydride. 0.4 ml, was added to a solution of 0.3 g of rac-2-[(2-aminophenyl)ethynyl]-3,4-dihydro-2,5,7,8-tetramethyl-2H,1-benzopyran-6ol in 25 ml of methylene chloride. The mixture was layered with 10 ml of 10% aqueous sodium carbonate solution and was stirred for 30 minutes at room temperature. The organic layer was separated, dried and evaporated. The residue was dissolved in hexane/ether, filtered and crystallized by cooling. The colorless crystals obtained had m.p. 116°–118°.

Anal. Calcd. for $C_{23}H_{22}F_3NO_3$: C, 66.18; H, 5.31; N, 3.56 Found: C, 66.24; H, 5.37; N, 3.27

EXAMPLE 45 rac-3,4-Dihydro-6-[(3,4-dihydro-6-hydroxy-2,5,7,8-tetramethyl2H-1-benzopyran-2-yl)ethynyl]-4(trifluoroacetyl)-2H-1,4-benzoxazine.

This compound was prepared by coupling rac-3,4-dihydro-2-ethynyl-2,5,7,8-tetramethyl-2H-1-benzopyran-6ol (1,15 g or 5 mmol) wi`h 4-(trifluoroacetyl)-3,4-dihydro-6-iodo 2H1,4-benzoxazine (1.95 g or 5.5 mmol) under the conditions described in Example 15. The product was isolated by chromatography over the 40 fold amount of silica gel methylene chloride. It was crystallized from ether/hexane and recrystallized twice from methanol to give colorless crystals with m.p. 153°–155°.

Anal. Calcd. for $C_{25}H_{24}F_3NO_4$: C, 65.35; H, 5.27; N, 3.05 Found: C, 65.21: H, 5.13; N, 3.09

The preparation of the starting material is described in Example 46.

EXAMPLE 46

4-(Trifluoroacetyl)-3,4-dihydro-6-iodo-2H-1,4-benzoxazine.

Trifluoroacetic anhydride 5.6 ml. was added to a solution of 4 g of 3,4-dihydro-2H-1,4-benzoxazine [H, Shirai et al. Nagoya Shiritsu Daigaku Takugakubu Kenkyu Nempo 17, 50 (1969)]in 50 ml of methylene chloride, layered with 75 ml of 10% aqueous sodium carbonate solution. The mixture was stirred in an ice bath for 30 minutes. The methylene chloride layer was separated, washed with brine, dried and evaporated. Crystallization from hexane gave 3,4-dihydro-4-(trifluoroacetyl)-2H-1,4-benzoxazine with m.p. 58°–60°.

A mixture of 0.5 g (2.16 mmol) of this 4-(trifluoroacetyl)-3,4-dihydro-2H-1,4-benzoxazine, 20 ml of glacial acetic acid and 5 ml of methylene chloride was cooled to 10° in an ice bath. A solution of 1 ml of iodine monochloride in 1 ml of acetic acid was added slowly over a period of 5 minutes Following the addition, the mixture was stirred for 45 minutes and was then diluted with water and a aqueous solution of sodium bisulfite. The product was extracted with ether. The extracts were washed with water, dried and evaporated. Crystallization of the residue from hexane yielded colorless crystals with m.p. 78°–80°.

Anal. Calcd. for $C_{10}H_7F_3INO_2$: C, 33.64H, 1.98; N, 3.92 Found: C, 33.56; H, 1.94; N, 4.01

EXAMPLE 47 rac-2-[(3,4-dihydro-2H-1,4-benzoxazine-6-yl)ethynyl]-3,4-dihydro-2,5,7,8-tetramethyl-2H-1-benzopyran-6-ol hydrochloride.

A solution of 0.3 g (0.6mmol) of rac-3,4-dihydro-6[(3,4-dihydro-6hydroxy-2,5,7,8-tetramethyl-2H-1-benzopyran-2-yl)ethynyl]-4-(trifluoroacetyl)-2H-1,4-benzoxazine in 25 ml of methanol was degassed with argon and treated with 0.5 ml of 3N sodium hydroxide solution. After stirring under argon for 30 minutes, the mixture was acidified with glacial acetic acid and evaporated under reduced pressure. The residue was partitioned between methylene chloride and saturated aqueous sodium bicarbonate solution. The organic layer was dried and evaporated. The residue was treated with ethanolic hydrogen chloride and crystallized by addition of ether to yield tan crystals with m.p. 150–°165° with decomposition. These crystals contained 0.33 molar equivalents of water.

Anal. Calcd. for $C_{23}H_{25}NO_3.HCl.0.33\ H_2O$: C, 68.05; H, 6.621 N, 3,45 Found: C, 68.34; H, 6.71; N, 3.41

EXAMPLE 48

6-(3,4-Dihydro-6-hydroxy-2,5,7,8-tetramethyl-2H-1-benzopyran-2-yl)ethynyl]-4-methyl-2H-1,4-benzoxazine-(4H)-one.

6[(3,4-dihydro-6-hydroxy-2,5,7,8-tetramethyl-2H-1-benzopyran-2-yl)ethynyl]-4-methyl-2H-1,4-benzoxazine-(4H)-one was similarly obtained by coupling rac-3,4-dihydro.2-ethynyl2,5,7,8-tetramethyl-2H-1-benzopyran-6ol (1.15 g or 5 mmol) with 1.6 g (5.5 mmol) of 6-iodo-4-methyl-2H-1,4-benzoxazine-3(4H)-one under the conditions described in Example 26. The compound was isolated from the reaction mixture by chromatography over the 40 fold amount of silica gel using 5% (V/V) of ethyl acetate in methylene chloride. It was crystallized and recrystallized from methanol to leave colorless crystals with m.p. 185°–188°.

Anal. Calcd. for $D_{24}H_{25}NO_4$: C, 73.64; H, 6.44; N, 3.58 Found: C, 73.38; H, 6.48; N, 3.63

The preparation of the required iodo compound is described in Example 49.

EXAMPLE 49

6-Iodo-4-methyl-2H-1,4-benzoxazine-(4H)-one.

A solution of 5 g of 4-methyl-2H-1,4-benzoxazine-3(4H)-one [Ref. in 100 ml of acetic acid and 25 ml of methylene chloride was cooled to 10°. Iodine monochloride, 15 ml, dissolved in 15 ml of acetic acid was added over 20 minutes while keeping the temperature between 10° and 15°. The reaction mixture was diluted with water and the excess reagent was reduced by addition of sodium bisulfite. The product was extracted with ether. The extracts were washed with aqueous sodium carbonate solution, dried and evaporated. Crystallization of the residue from ether gave colorless crystals with m.p. 146°–148°.

Anal. Calcd. for $C_9H_8INO_2$: C, 37.40; H, 2.79; N, 4.85 Found: C, 37.16; H, 2.70; N, 4.74.

EXAMPLE 50 rac-3,4-Dihydro-2-[(2-hydroxyphenyl)ethynyl]-2,5,7,8-tetramethyl-2H-1-benzopyran-6-ol and rac-2-(2-Benzofuranyl)-3,4-dihydro-2,5,7,8-tetramethyl-2H-1-benzopyran-6-ol.

Reaction of rac-3,4-dihydro-2-ethynyl-2,5,7,8-tetramethyl-2H-1-benzopyran-6-ol with 2-iodophenol under the conditions described in Example 14 and the reaction time extended to 4 days gave a mixture of the two title compounds. They were separated by chromatography over the 40-fold amount of silica gel using methylene chloride. The less polar 2-(2-benzofuranyl)-3,4-dihydro-2,5,7,8-tetramethyl-2H-1-benzopyran-6-ol was crystallized from ether hexane to give colorless crystals with m.p. 90°–93°.

Anal. Calcd. for $C_{21}H_{22}O_3$: C, 78.23; H, 6.88 Found: C, 78.55; H, 6.88

The more polar rac-3,4-dihydro-2-[(2-hydroxyphenyl)-ethynyl]-2,5,7,8-tetramethyl-2H-1-benzopyran-6-ol was crystallized from ether/hexane and recrystallized again from hexane to yield colorless crystals with m.p. 123°–125°.

Anal. Calcd. for $C_{21}H_{22}O_3$: C, 78.23; H, 6.88 Found: C, 77.62; H, 6.81

EXAMPLE 51 rac-3,4-Dihydro-2-(5-methylfuro[3,2[b]pyridin-2-yl)-2,5,7,8-tetramethyl-2H-1-benzopyran-6ol.

The title compound was obtained by coupling rac-3,4-dihydro-2-ethynyl-2,5,7,8-tetramethyl-2H-1-benzopyran-6-ol with 2-iodo-3-hydroxy-6-methylpyridine under the conditions described in Example 26 but by using double the amount of triethylamine and extending the reaction time to 3 days. The product was isolated by chromatography over the 40-fold amount of silica gel using 10% (V/V) of ethyl acetate in methylene chloride. Crystallization of the combined clean fractions from ether/hexane gave colorless crystals with m.p. 115–118°.

Anal. Calcd. for $C_{21}H_{23}NO_3$: C,. 74.75; H, 6.87; N, 4.15 Found: C, 74.56: H, 6.82; N, 4.10

EXAMPLE 52 rac-3,4-Dihydro-2-(furo[3,2-b]pyridine-2-yl)-2,5,7,8-tetramethyl-2H-1-benzopyran-6-ol.

This compound was prepared by reacting rac-3,4-dihydro-2-ethynyl-2,5,7,8-tetramethyl-2H-1-benzopyran-6-ol with 2-bromo-3-hydroxypyridine under the conditions described in Example 26, but using twice as much triethylamine and lengthening the reaction time to 3 days. Chromatography of the crude product over the 40-fold amount of silica gel using 10 % (V/V) of ethyl acetate in methylene chloride followed by crystallization from ether/hexane and recrystallization from ethyl acetate/hexane gave off-white crystals with m.p. 168°–169°.

Anal. Calcd. for $C_{20}H_{21}NO_3$: C, 74.28; H, 6.55; N, 4.23 Found: C, 74.59; H, 6.46; N, 4.28

EXAMPLE 53 rac-1-2-(3,4-Dihydro-6-hydroxy-2,5,7,8-tetramethyl-2H-1-benzopyran-2-yl)-6-hydroxy-7-propylbenzofuran-5-yl]ethanone.

The title compound was obtained by coupling rac-3,4-dihydro-2-ethynyl-2,5,7,8-tetramethyl-2H-1-benzopyran-6-ol with 1-(2,4-dihydroxy-5-iodo-3-propylphenyl)ethanone [J. Rokach et al. U.S. Pat. No. 4,252,818; Febr. 1981]under the conditions described in Example 26 by extending the reaction time to 48 hours and doubling the amount of triethylamine. The product was isolated by chromatography and was crystallized in the freezer from ether/hexane. The analytical sample was recrystallized from the same solvents and had m.p. 121°-124°.

Anal. Calcd. for $C_{26}H_{30}O_5$: C, 73.91; H, 7.16 Found: C, 73.35; H, 7.11

EXAMPLE 54 rac-2-(3,4-Dihydro-6-hydroxy-2,5,7,8-tetramethyl-2H-1-benzopyran-2-yl)-7-methoxy-5-benzofurancarboxaldehyde.

The title compound was obtained by reacting rac-3,4-dihydro-2-ethynyl-2,5,7,8-tetramethyl-2H-1-benzopyran-6-ol with 3 iodo-4-hydroxy-5-methoxybenzaldehyde under the conditions described in Example 26 but using twice as much triethylamine and lengthening the reaction time to 48 hours. The product was isolated by chromatography over the 40 fold amount of silica gel using 10% (V/V) of ethyl acetate in methylene chloride and by rechromatography over the 50 fold amount of silica gel using methylene chloride. Crystallization of the combined clean fractions from ether/hexane in the freezer followed by recrystallization from ethyl acetate/hexane gave colorless crystals with m.p. 124°-127°.

Anal. Calcd. for $C_{23}H_{24}O_5$: C, 72.61; H, 6.36 Found: C, 72.52; H, 6.40

EXAMPLE 55 rac-2-(3,4-Dihydro-6-hydroxy-2,5,7,8-tetramethyl-2H-1-benzopyran-2-yl)-7-methoxybenzofuran-5-methanol.

A mixture of 0.2 g of rac-2-(3,4-dihydro 6-hydroxy-2,5,7,8-tetramethyl-2H-1-benzopyran-2-yl) -7-methoxy-5-benzofurancarboxaldehyde and 20 mg of sodium borohyride in 5 ml of ethanol was stirred under nitrogen for 30 minutes. It was partitioned between methylene chloride and saturated aqueous sodium bicarbonate solution. The organic layer was separated. dried over sodium sulfate and evaporated. Crystallization from ether/hexane yielded colorless crystals with m.p. 122°-125°.

Anal. Calcd. for $C_{23}H_{26}O_5$: C, 72.23; H, 6.85 Found: C, 71.98; H, 6.80.

EXAMPLE 56

3,4-Dihydro-2,5,7,8-tetramethyl-2-(2-phenylethyl)-2H-1-benzopyran-6-ol.

A mixture of 1.3 g (4.2 mmol) of 3,4-dihydro-2,5,7,8-tetramethyl-2-(2-phenylethynyl)-2H-1-benzopyran-6-ol (Example 1), 0.3 g of 5 % palladium on carbon. 50 ml of tetrahydrofuran and 50 ml ethanol was hydrogenated at atmospheric pressure for 4 hours. The catalyst was filtered off and the filtrate was evaporated. Crystallization of the residue from hexane yielded 0.9 g (69 %) of colorless crystals with m.p. 96°-98°.

Anal. Calcd. for $C_{21}H_{22}O_2$: C, 82.32; H, 7.24 Found: C, 82.02; H, 7.30

EXAMPLE 57 rac-3,4-Dihydro-2,5,7,8-tetramethyl-2-[2-(2-thienyl)ethyl]-2H-1-benzo-pyran-6-ol.

Hydrogenation of rac-3,4-dihydro-2,5,7,8-tetramethyl-2-[2-(2-thienyl)-ethynyl]-2H-1-benzopyran-6ol as described in Example 56 gave the title compound, crystallized from hexane with m.p. 95°-98°.

Anal. calcd. for $C_{19}H_{24}O_2S$: C, 72.11; H, 7.64 Found: C, 71.99; H, 7.61

EXAMPLE 58 rac-3,4-Dihydro-2,5,7,8-tetramethyl-2-[2-(2-pyridinyl)ethyl]-2H-1-benzopyran-6-ol.

This compound was similarly prepared by hydrogenation of rac-3,4-dihydro-2,5,7,8-tetramethyl 2 -[2-(2-pyridinyl)ethynyl]-2H-1-benzopyran-6-ol as described in Example 56. The product crystallized from ethyl acetate/hexane and had m.p. 141°-142°.

Anal. Calcd. for $C_{20}H_{25}NO_2$: C, 77.14; H, 8.09; N, 4.50 Found: C, 77.02; H, 8.14; N, 4.49

EXAMPLE 59 rac-3,4-Dihydro-2,5,7,8-tetramethyl-2-[2-(3-pyridinyl)ethyl]-2H-1-benzopyran-6-ol.

Hydrogenation of rac-3,4-dihydro-2,5,7,8-tetramethyl-2-[2-(3-pyridinyl)ethynyl]-2H-1-benzopyran-6ol under the conditions described in Example 56 gave the title compound, crystallized from ether/hexane and recrystallized from ethyl acetate/hexane. The colorless crystals melted at 127°-129°.

Anal. calcd. for $C_{20}H_{25}NO_2$: C, 77.14; H, 8.09; N, 4.50 Found: C, 76.50; H, 8.11; N 4.66

EXAMPLE 60 rac-2-{2-[3-(Acetyloxy)-4-methoxyphenyl]ethyl}-3,4-dihydro-2,5,7,8-tetramethyl-2H-1-benzopyran-6ol.

A mixture of 0.7 g of rac-2-{2-[3-(acetyloxy)-4 -methoxyphenyl]ethynyl}-3,4-dihydro-2,5,7,8-tetramethyl-2H-1-benzopyran-6-ol, 0.2 g of 5 % palladium on carbon and 50 ml of ethanol was hydrogenated at atmospheric pressure for 2 hours. The catalyst was removed by filtration and the filtrate was evaporated. Crystallization from ether/hexane gave 0.6 g of colorless crystals with m.p. 110°-113°.

Anal. calcd. for $c_{24}H_{30}O_5$: C, 72.34; H, 7.59 Found: C, 72.22; H, 7.65

EXAMPLE 61 rac-4-[2-(3,4-Dihydro-6-hydroxy-2,5,7,8-tetramethyl-2H-1-benzopyran-2-yl)ethyl]-1,2-benzenediol.

A mixture of 1 g of rac-3,4-dihydro-2-{[3-hydroxy-4-(phenylmethoxy)phenyl]ethynyl}-2,5,7,8-tetramethyl-2H-1-benzopyran-6-ol, 0.5 g of 5% palladium on carbon. 100 ml of ethanol and 10 ml of glacial acetic acid was hydrogenated at atmospheric pressure for 4.5 hours. The catalyst was filtered off and the filtrate was evaporated. The residue was partitioned between methylene chloride and saturated sodium bicarbonate solution. The organic layer was dried and evaporated and the residue was crystallized from ether/hexane to give 0.5 g of colorless crystals with m.p. 167°-170°.

Anal. Calcd. for $C_{21}H_{26}O_4$: C, 73.66; H, 7.65 Found : C, 73,40; H, 7.71

EXAMPLE 62 rac-3,4-Dihydro-2-[2-(3-methoxyphenyl)ethyl]-2,5,7,8-tetramethyl-2H-1-benzopyran-6-ol.

This compound was obtained by hydrogenation of rac-3,4-dihydro-2-[2-(3-methoxyphenyl)ethynyl]-2,5,7,8-tetramethyl-2H-1-benzopyran-6ol under the conditions described in Example 56, but extending the time to 8 hours. The product was crystallized from ether/hexane to leave colorless crystals with m.p. 105°–107°.

Anal. Calcd. for $C_{22}H_{28}O_3$: C. 77.61; H, 8.29 Found: C. 77.61; H, 8.52

EXAMPLE 63 rac-5-[2-(3,4-Dihydro-6-hydroxy-2,5,7,8-tetramethyl-2H-1-benzopyran-2-yl) ethyl]-2-hydroxybenzoic acid methyl ester.

A mixture of 0.7 g of rac-5-[2-(3,4-dihydro-6-hydro2,5,7,8-tetramethyl-2H-1-benzopyran-2-yl)ethynyl]-2-hydroxybenzoic acid methyl ester, 0.2 g of 5% palladium on carbon and 20 ml of methanol was hydrogenated at atmospheric pressure for 4 hours. The catalyst was separated by filtration and the filtrate was evaporated. The residue was passed over 10 g of silica gel (70–230 mesh) using methylene chloride. The product was crystallized from ether/hexane to give 0.5 g of colorless crystals with m.p. 108°–110°.

Anal. calcd. for $C_{23}H_{28}O_5$: C, 71.85; H, 7.34 Found: C, 71.93; H, 7.49

EXAMPLE 64 rac-3,4-Dihydro-2,5,7,8-tetramethyl-2-{2-[4-(3-pyridinyl)-phenyl]ethyl}-2H-1-benzopyran-6-ol.

Hydrogenation of rac-3,4-dihydro-2,5,7,8-tetramethyl-2-{2-[4-(3-pyridinyl)phenyl]ethynyl}-2H-1-benzopyran-6-ol under the conditions described in Example 56 yielded the title compound which was crystallized from ethyl acetate and had m.p. 175°–178°.

Anal. calcd. for $C_{26}H_{29}NO_2$: C, 80.59; H, 7.54; N, 3.61 Found: C. 80.23; H, 7.69: N, 3.64

EXAMPLE 65 rac-3,4-Dihydro-2,5,7,8-tetramethyl-2-{2-[5-(2-pyridinyl)-2-thienyl]ethyl}-2H-1-benzopyran-6ol.

This compound was prepared by hydrogenating rac-3,4-dihydro-2,5,7,8-tetramethyl-2-{2-[5-2-pyridinyl)-2-thienyl]-ethynyl}-2H-1-benzopyran-6-ol under conditions used in Example 56. The product was crystallized from ether/hexane o and was recrystallized from ethanol to give colorless crystals with m.p. 140°–142°.

Anal calcd. for $C_{24}H_{27}NO_2S$: C, 73.25; H, 6.92; N, 3.56 Found: C, 72.96; H, 7.00; N, 3.52

EXAMPLE 66 rac-2-[2-(5-Butyl-2-thienyl)ethyl]-3,4-dihydro-2,5,7,8-tetramethyl-2H-1-benzopyran-6-ol.

Hydrogenation of rac-2-[2-(5-butyl-2-thienyl)ethynyl]-3,4-dihydro-2,5,7,8-tetramethyl-2H -1-benzopyran-6ol for 6.5 hours under the conditions of Example 56 yielded the title compound which was crystallized from petroleum ether and had m.p. 83°–85°.

Anal. calcd. for $C_{23}H_{32}O_2S$: C, 74.15; H, 8.66 Found: C, 74.06: H, 8.58

EXAMPLE 67 rac-4-[2-(3,4-Dihydro-6-hydroxy-2,5,7,8-tetramethyl-2H-1-benzopyran-2-yl)ethyl]-1,2-benzenediol-2-acetate.

A mixture of 0.94 g (2 mmol) of rac-2-{[3-acetyloxy4-(phenylmethoxy)phenyl]ethynyl}-3,4-dihydro-2,5,7,8-tetramethyl-2H-1-benzopyran-6-ol, 0.5 g of 5% palladium on carbon. 50 ml of ethanol and 2 ml of glacial acetic acid was hydrogenated at atmospheric pressure for 4 hours.

The catalyst was filtered off and the filtrate was evaporated. The residue was partitioned between methylene chloride and saturated aqueous sodium bicarbonate solution. The organic layer was dried and evaporated and the residue was crystallized from ether/hexane to give colorless crystals with m.p. 139°–141°.

Anal. calcd. for $c_{23}H_{28}O_5$: C, 71.85; H, 7.34 Found: C, 71.48; H, 7.30

EXAMPLE 68 rac-{2-[5-(Aminomethyl)-2-hydroxy-3-methoxyphenyl]ethyl}-3,4-dihydro-2,5,7,8-tetramethyl-2H-1-benzopyran-6-ol hydrochloride.

A mixture of 0.3 g of rac-3-[{3,4-dihydro-6-hydroxy-2,5,7,8-tetramethyl-2H-1-benzopyran-2yl)ethynyl]-4-hydroxy-5-methoxybenzaldehyde oxime, 0.15 g of palladium on carbon (5%) and 20 ml of ethanol was hydrogenated at atmospheric pressure for 3 hours. The catalyst was removed by filtration and the residue was treated with ethanolic hydrogen chloride and crystallized by addition of ethyl acetate and ether. Recrystallization from methanol/ethyl acetate gave colorless crystals with m.p. 164°–167° dec.

Anal. calcd. for $C_{23}H_{31}NO_4 \cdot HCl$: C. 65.47; H, 7.64; N, 3.32 Found: C, 64.88; H, 7.72; N, 3.26

EXAMPLE 69 rac-6-Acetyloxy-3,4-dihydro-2,5,7,8-tetramethyl-2-(phenyl-ethynyl)-2H-1-benzopyran.

A mixture of 0.3 g of rac-3,4-dihydro-2,5,7,8-tetramethyl-2-(phenylethynyl)-2H-1-benzopyran-6-ol, 7 ml of pyridine and 0.5 ml of acetic anhydride was allowed to sit at room temperature over night. The reagents were evaporated under reduced pressure, at the end azeotropically with toluene. The residue was crystallized from hexane to give 0.21 g of colorless crystals with m.p. 123°–125°.

Anal. calcd. for $c_{23}H_{24}O_3$: C, 79.28; H, 6.94 Found: C, 79.18; H, 6.84

EXAMPLE 70 rac-6-Acetyloxy-2-[(benzo[b]thiophen-3-yl)ethynyl]-3,4-dihydro-2,5,7,8-tetramethyl-2H-1-benzopyran.

A mixture of 0.3 g of rac-2-[(benzo[b]thiophen-3-yl)ethynyl]-3,4-dihydro-2,5,7,8-tetramethyl-2H-1-benzopyran-6ol, 20 ml of pyridine and 1 ml of acetic anhydride was allowed to. sit at room temperature over night and was then evaporated to dryness under reduced pressure. The residue was crystallized from hexane to yield 0.25 g of colorless crystals with m.p. 99°–101°.

EXAMPLE 71 rac-(Z)-3,4-Dihydro-2,5,7,8-tetramethyl-2-[(2-pyridinyl)-ethenyl]-2H-1-benzopyran-6-ol hydrochloride.

A mixture of 0.3 g of rac-3,4-dihydro-2,5,7,8-tetramethyl-2-[(2-pyridinyl)ethynyl]-2H-1-benzopyran-6-ol, 0.15 g of 5% palladium on carbon, 20 ml of tetrahydrofuran, 10 ml of ethanol and 0.2 ml of thiophene was hydrogenated at atmospheric pressure for 2 hours. The catalyst was separated by filtration and the residue was chromatographed over 10 g of silica gel (Merck 230–400 mesh) using hexane:tetrahydro furan 2:1 for elution. The clean fractions containing the product were combined and evaporated. The residue was converted to a crystalline hydrochloride, crystallized from methanol ether, with m.p. 218°–220°.

EXAMPLE 72 rac-6-Acetyloxy-2-(benzo[b]thiophen-3-yl)ethynyl-3,4-dihydro-2,5,7,8-tetramethyl-2H-1-benzopyran.

A mixture of 0.544 g of rac-6-acetyloxy-2-ethynyl3,4-dihydro-2,5,7,8-tetramethyl-2H-1-benzopyran, 0.64 g of 3-bromobenzothiophene, 90 mg of triphenylphosphine, 20 mg of cuprous iodide, 2 ml of triethylamine and 40 ml of dimethylformamide was stirred and degased by a stream of argon for 15 minutes. Palladium acetate, 30 mg, was then added and the mixture was heated at 95° C. for 5 hours. The reaction mixture was partitioned between saturated sodium bicarbonate solution and toluene. The organic phase was washed with water, dried and evaporated. The residue was chromatographed over 50 g of silica gel using toluene for elution. The combined clean fractions were crystallized from hexane to give the title compound with m.p. 96–99°.

EXAMPLE 73

| TABLET FORMULATION (Wet Granulation) | | | |
|---|---|---|---|
| Item | Ingredient | 100 mg | 500 mg |
| 1. | rac-[2-(benzo[b]thiophen-3-yl)ethynyl]-3,4-dihydro-2,5,7,8-tetramethyl-2H-1-benzopyran-6-ol | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | TOTAL | 167 | 836 |

Manufacturing procedure:

1) Mix items 1, 2, 3 and 4 and granulate with water.
2) Dry the granulation at 50° C.
3) pass the granulation through suitable milling equipment.
4) Add Item 5 and mix for three minutes; compress on a suitable press.

EXAMPLE 74

| CAPSULE FORMULATION | | | |
|---|---|---|---|
| Item | Ingredient | 100 mg | 500 mg |
| 1. | rac-[2-(benzo[b]thiophen-3-yl)ethynyl]-3,4-dihydro-2,5,7,8-tetramethyl-2H-1-benzopyran-6-ol | 100 | 500 |
| 2. | Corn Starch (Pregelantinized) | 8 | 40 |
| 3. | Modified Starch | 4 | 20 |
| 4. | Talc | 4 | 20 |
| 5. | Magnesium Stearate | 1 | 2 |
| | TOTAL | 117 | 582 |

Manufacturing procedure:

1) Mix Items 1, 2, and 3 and wet granulate with water. Dry at 45° C. overnight.
2) Mill through suitable screen using appropriate milling equipment.
3) Add Items 4 and 5 and mix for five minutes.

EXAMPLE 75

| INHALATION AEROSOL FORMULATION (SUSPENSION) | | |
|---|---|---|
| Item | Ingredients | % w/w |
| 1. | rac-[2-(benzo[b]thiophen-3-yl)ethynyl]-3,4-dihydro-2,5,7,8-tetramethyl-2H-1-benzopyran-6-ol (micronized) | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing procedure:

1) Mix Items 1 and 2 into 4 and homogenize.
2) Fill the concentrate suspension form Step 1 into a suitable can and place in valve and crimp to seal container.
3) pressure-fill a 80:20 mixture of Items 3 and 5.

NOTE: A suitable valve may be used to deliver 25 to 100 microliters in volume.

EXAMPLE 76

| CREAM 0.5% The following is the quantitative composition of drug: | | |
|---|---|---|
| Ingredients | g/kg | Reasonable Variations |
| rac-[2-(benzo[b]thiophen-3-yl)ethynyl]-3,4-dihydro-2,5,7,8-tetramethyl-2H-1-benzopyran-6-ol | 5.150* | — |
| Glyceryl Monostearate S.E.(1) | 100.00 | 80–120 |
| Polysorbate 60(2) | 20.00 | 15–25 |
| Cetyl Alcohol | 50.00 | 40–60 |
| Petrolatum | 70.00 | 50–90 |
| Methylparaben | 1.50 | 1.25–1.75 |
| Propylparaben | 0.50 | 0.4–0.6 |
| Propylene Glycol | 200.00 | 150–250 |
| Purified Water | 568.05 | 475–575 |
| TOTAL | 1,015.20 | |

Manufacturing procedure:

1) Dissolve rac-[2-(benzo[b]thiophen-3-yl)ethynyl]-3,4-dihydro-2,5,7,8-tetramethyl-2H-1-benzopyran-6-ol in propylene glycol, add methyl paraben, propyl paraben and water and heat to 70° C.
2) Melt petrolatum, glyceryl monostearate S.E., and cetyl alcohol. Heat to 70° C. Add polysorbate 80 and mix. Add solution in step 2 to solution in step 1 at 70° C. cool to room temperature while stirring.

*3% excess (1) Arlacel 165

(2) Tween 60

I claim:

1. A racemic compound of the formula

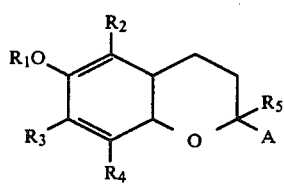

wherein

A is—C≡C—R$_6$

R$_1$ is hydrogen or lower alkanoyl,

R$_2$, R$_3$, and r$_4$ independently are hydrogen or lower alkyl,

R$_5$ is lower alkyl,

R$_6$ is a heteroaromatic radical selected from pyridinyl, imidazoyl, thienyl, 2-(pyridyl)thienyl, 2-(phenyl)thienyl, 2-chlorothienyl, furyl, pyrimidinyl, oxazolyl, quinolinyl, isoquinolinyl, indolyl, benzothienyl or benzofuranyl or an aromatic radical selected from phenyl, naphthyl or phenanthryl, which aromatic radical may optionally be substituted by one or more substituents selected from chlorine, fluorine, lower alkyl, lower alkoxy, phenyl lower alkoxy, lower alkanoyl, lower alkanoyloxy, hydroxy-lower alkyl, carboxy, lower alkoxycarbonyl, hydroxyimino lower alkyl, amino, amino lower alkyl, mono- or di-lower alkyl amino, mono- or di-lower alkylamino-lower alkyl, lower alkanoylamino, aminocarbonyl, lower alkylaminocarbonyl, lower dialkylaminocarbonyl, trifluoroacetylamino, trifluoromethyl, hydroxy, pyridyl, or on adjacent carbons can be

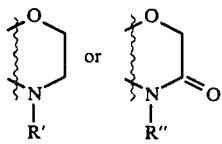

wherein R' is hydrogen, lower alkanoyl, trifluoroacetyl and R" hydrogen or lower alkyl, or an enantiomer thereof or a salt thereof.

2. A compound, in accordance with claim 1, wherein R$_1$ is hydrogen, and R$_2$–R$_5$ are methyl.

3. A compound, in accordance with claim 1, wherein R$_1$ is hydrogen, R$_2$–R$_5$ are methyl and R$_6$ is unsubstituted phenyl, thienyl, benzothienyl or pyridinyl or substituted phenyl.

4. A compound, in accordance with claim 1, wherein R$_1$ is hydrogen, and R$_2$–R$_5$ are lower alkyl.

5. A compound, in accordance with claim 1, R-[2-(Benzo[b]thiophene-3yl)ethynyl]-3,4-dihydro-2,5,7,8-tetramethyl-2H-1-benzopyran-6-ol.

6. A compound, in accordance with claim 1, S-[2-(Benzo[b]thiophene-3yl)ethynyl]-3,4-dihydro-2,5,7,8-tetramethyl-2H-1-benzopyran-6ol.

7. A compound, in accordance with claim 1, rac-[2-(Benzo[b]thiophene-3-yl)ethynyl]-3,4-dihydro-2,5,7,8-tetramethyl-2H-1-benzopyran-6-ol.

8. A compound, in accordance with claim 1, R-3,4-Dihydro-2,5,7,8-tetramethyl-2[(2-thienyl)ethynyl]-2H-1-Benzopyran -6-ol.

9. A compound, in accordance with claim 1, S-3,4-Dihydro-2,5,7,8-tetramethyl-2[(2-thienyl)ethynyl]-2H-1-benzopyran-6-ol.

10. A compound, in accordance with claim 1, rac-3,4-Dihydro-2,5,7,8-tetramethyl-2[(2-thienyl)ethynyl]-2H-1-benzopyran-6-ol.

11. A pharmaceutical composition comprising an effective amount of a racemic compound of the formula

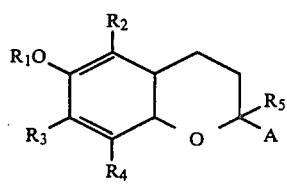

wherein

A is —C≡C—R$_6$,

R$_1$ is hydrogen or lower alkanoyl,

R$_2$, R$_3$, and R$_4$ independently are hydrogen or lower alkyl,

R$_5$ is lower alkyl,

R$_6$ is a heteroaromatic radical selected from pyridinyl, imidazolyl, thienyl, 2-(pyridyl)thienyl, 2-(phenyl)thienyl, 2-chlorothienyl, furyl, pyrimidinyl, oxazolyl, quinolinyl, isoquinolinyl, indolyl, benzothienyl or benzofuranyl, or an aromatic radical selected from phenyl, naphthyl or phenanthryl, which aromatic radimal may optionally be substituted by one or more substituents selected from chlorine, fluorine, lower alkyl, lower alkoxy, phenyl lower alkoxy, lower alkanoyl, lower alkanoyloxy, hydroxy-lower alkyl, carboxy, lower alkoxycarbonyl, hydroxyimino lower alkyl, amino, amino lower alkyl, mono- or di- lower alkyl amini, mono- or di-lower alkylamino-lower alkyl, lower alkanoylamino aminocarbonyl, lower alkylaminocarbonyl, lower dialkylaminocarbonyl, trifluoroacetylamino, trifluoromethyl, hydroxy, pyridyl, or an adjacent carbons can be

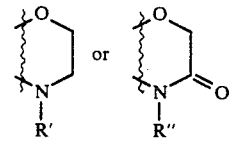

wherein R' is hydrogen, lower alkanoyl, trifluorocetyl and R" hydrogen or lower alkyl, or an enantiomer thereof or a salt thereof, and an inert carrier.

12. A pharmaceutical composition, in accordance with claim 11, wherein R$_1$ is hydrogen, and R$_2$–R$_5$ are methyl.

13. A pharmaceutical composition, in accordance with claim 11, wherein R$_1$ is hydrogen, R$_2$–R$_5$ are methyl and R$_6$ is unsubstituted phenyl, thienyl, benzothienyl or pyridinyl or substituted phenyl.

14. A pharmaceutical composition, in accordance with claim 11, wherein R$_1$ is hydrogen, and R$_2$–R$_5$ are lower alkyl.

15. A pharmaceutical composition, in accordance with claim 11, wherein the compound of formula I is R-[2-(benzo[b]thiophene-3-yl)ethynyl]-3,4-dihydro-2,5,7,8-tetramethyl-2H-1-benzopyran-6-ol.

16. A pharmaceutical composition, in accordance with claim 11, wherein the compound of formula I is S-[2-(benzo[b]thiophene-3-yl)ethynyl]-3,4-dihydro-2,5,7,8-tetramethyl-2H-1-benzopyran-6ol.

17. A pharmaceutical composition, in accordance with claim 11, wherein the compound of formula I is rac-[2-(benzo[b]thiophene-3-yl)ethynyl]-3,4-dihydro-2,5,7,8-tetramethyl-2H-1-benzopyran-6ol.

18. A pharmaceutical composition, in accordance with claim 11, wherein the compound of formula I is R-3,4-Dihydro2,5,7,8-tetramethyl-2-[(2-thienyl)ethynyl]-2H-1-benzopyran-6ol.

19. A pharmaceutical composition, in accordance with claim 11, wherein the compound of formula I is S-3,4-Dihydro2,5,7,8-tetramethyl-2[(2-thienyl)ethynyl]-2H-1-benzopyran-6ol.

20. A pharmaceutical composition, in accordance with claim 11, wherein the compound of formula I is rac-3,4-Dihydro-2,5,7,8-tetramethyl-2-[(2-thienyl)ethynyl]-2H-1-benzopyran-6-ol.

21. A method of treating disease states caused or aggravated by excessive oxidative metabolism of arachidonic acid which comprises administering to a host requiring such treatment an effective amount of racemic compound of formula

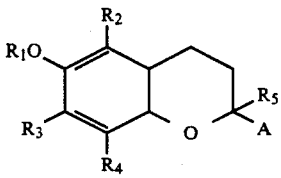

wherein
A is —C≡C—R$_6$,
R$_1$ is hydrogen or lower alkanoyl,
R$_2$, R$_3$, and R$_4$ independently are hydrogen or lower alkyl,
R$_5$ is lower alkyl,
R$_6$ is a heteroaromatic radical selected from pyridinyl, imidazolyl, thienyl, 2-(pyridyl) thienyl, 2-(phenyl)thienyl, 2-chlorothienyl, furyl, pyrimidinyl, oxazolyl, quinolinyl, isoquinolinyl, indolyl, benzothienyl or benzofuranyl, or an aromatic radial selected from phenyl, naphthyl or phenanthryl, which aromatic radical may optionally be substituted by one or more substitutents selected from chlorine, fluorine, lower alkyl, lower alkoxy, phenyl lower alkoxy, lower alkanoyl, lower alkanoyloxy, hydroxy-lower alkyl, carboxy, lower alkoxycarbonyl, hydroxyimino lower alkyl, amino, amino lower alkyl, mono- or di- lower alkyl amino, mono- or di-lower alkylamino-lower alkyl, lower alkanoylamino, amionocarbonyl, lower alkylaminocarbonyl, lower dialkylaminocarbonyl, trifluoroacetylamino, trifluoromethyl, hydroxy, pyridyl, or on adjacent carbons can be

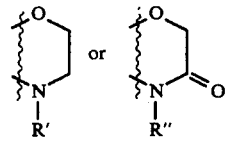

wherein R' is hydrogen, lower alkanoyl, trifluoroacetyl and R" hydrogen or lower alkyl,
or an enantiomer thereof or a salt thereof.

22. A method in accordance with claim 21, wherein R$_1$ is hydrogen, and R$_2$-R$_5$ are methyl.

23. A method in accordance with claim 21, wherein R$_1$ is hydrogen, R$_2$-r$_5$ are methyl and R$_6$ is unsubstituted phenyl, thienyl, benzothienyl or pyridinyl or substituted phenyl.

24. A method in accordance with claim 21, wherein R$_1$ is hydrogen, and R$_2$-R$_5$ are lower alkyl.

25. A method in accordance with claim 21, wherein the compound of formula I is R-[2-(Benzo[b]thiophene-3-yl) ethynyl]-3,4-dihydro-2,5,7,8-tetramethyl-2H-1-benzopyran-6-ol.

26. A method in accordance with claim 21, wherein the compound of formula I is S-[2-(Benzo[b]thiophene-3-yl) ethynyl]-3,4-dihydro-2,5,7,8-tetramethyl-2H-1-benzopyran-6-ol.

27. A method in accordance with claim 21, wherein the compound of formula I is rac-[2-(Benzo[b]thiophene-3-yl) ethynyl]-3,4-dihydro-2,5,7,8-tetramethyl-2H-1-benzopyran-6-ol.

28. A method in accordance with claim 21, wherein the compound of formula I is R-3,4-Dihydro-2,5,7,8-tetramethyl-2[(2-thienyl)ethynyl]-2H-1-benzopyran-6-ol.

29. A method in accordance with claim 21, wherein the compound of formula I is S-3,4-Dihydro-2,5,7,8-tetramethyl-2[(2-thienyl)ethynyl]-2H-1-benzopyran-6-ol.

30. A method in accordance with claim 21, wherein the compound of formula I is rac-3,4-Dihydro-2,5,7,8-tetramethyl -2[(2-thienyl)ethynyl]-2H-1-benzopyran-6-ol.

* * * * *

UNITED STATES PATENT AND TRADEMARK OFFICE
CERTIFICATE OF CORRECTION

PATENT NO. : 5,015,661
DATED : May 14, 1991
INVENTOR(S) : Armin Walser It is certified that error appears in the above-identified patent and that said Letters Patent is hereby corrected as shown below:

Claim 1, Column 43, line 16, "$r_4$" should be --- $R_4$ --- .

Claim 11, Column 44, line 31, "radimal" should be --- radical --- .

Claim 11, Column 44, line 37, "amini" should be --- amino --- .

Claim 21, Column 45, lines 45-46, "radial should be --- radical --- .

Claim 21, Column 46, line 5, "amionocarbonyl" should be --- aminocarbonyl --- .

Claim 23, Column 46, line 23, "$R_2-r_5$" should be --- $R_2-R_5$ --- .

Signed and Sealed this

Sixth Day of July, 1993

*Attest:*

MICHAEL K. KIRK

*Attesting Officer*   Acting Commissioner of Patents and Trademarks